(12) United States Patent
Abbott et al.

(10) Patent No.: US 12,318,406 B2
(45) Date of Patent: **\*Jun. 3, 2025**

(54) METHODS OF TREATMENT USING TOPICAL COPPER ION FORMULATIONS

(71) Applicant: CDA Research Group, Inc., Pittsburgh, PA (US)

(72) Inventors: ChunLim Abbott, Pittsburgh, PA (US); Dominic C. Abbott, Pittsburgh, PA (US)

(73) Assignee: CDA RESEARCH GROUP, INC., Pittsburgh, PA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 16/797,580

(22) Filed: Feb. 21, 2020

(65) Prior Publication Data

US 2020/0206264 A1 Jul. 2, 2020

Related U.S. Application Data

(63) Continuation-in-part of application No. 15/865,995, filed on Jan. 9, 2018, now Pat. No. 10,813,948, which is a continuation of application No. 15/265,570, filed on Sep. 14, 2016, which is a continuation-in-part of application No. 13/841,992, filed on Mar. 15, 2013, and a continuation-in-part of application No. 13/841,882, filed on Mar. 15, 2013, now abandoned, and a continuation-in-part of application No. 13/842,310, filed on Mar. 15, 2013, and a continuation-in-part of application No. 13/842,387, filed on Mar. 15, 2013, now Pat. No. 10,398,733.

(51) Int. Cl.
| | |
|---|---|
| *A61K 9/06* | (2006.01) |
| *A01M 31/00* | (2006.01) |
| *A61K 8/19* | (2006.01) |
| *A61K 9/00* | (2006.01) |
| *A61K 9/02* | (2006.01) |
| *A61K 9/08* | (2006.01) |
| *A61K 9/10* | (2006.01) |
| *A61K 9/12* | (2006.01) |
| *A61K 9/70* | (2006.01) |
| *A61K 33/34* | (2006.01) |
| *A61P 17/00* | (2006.01) |
| *A61P 17/02* | (2006.01) |
| *A61Q 11/00* | (2006.01) |
| *A61Q 17/00* | (2006.01) |
| *A61Q 19/00* | (2006.01) |

(52) U.S. Cl.
CPC ............ *A61K 33/34* (2013.01); *A01M 31/00* (2013.01); *A61K 8/19* (2013.01); *A61K 9/0014* (2013.01); *A61K 9/0031* (2013.01); *A61K 9/0034* (2013.01); *A61K 9/0036* (2013.01); *A61K 9/0043* (2013.01); *A61K 9/0046* (2013.01); *A61K 9/006* (2013.01); *A61K 9/02* (2013.01); *A61K 9/06* (2013.01); *A61K 9/08* (2013.01); *A61K 9/10* (2013.01); *A61K 9/12* (2013.01); *A61K 9/122* (2013.01); *A61K 9/7084* (2013.01); *A61Q 11/00* (2013.01); *A61Q 17/005* (2013.01)

(58) Field of Classification Search
CPC ........ A61K 45/06; A61K 9/0014; A61K 9/06; A61K 33/34; A61K 9/08; A61K 9/02; A61K 9/122; A61K 31/08; A61P 1/04; A61P 17/00; A61P 17/02; A61Q 19/00; A61Q 19/08; A61Q 17/005; A61Q 17/04; A61Q 19/004; A01N 59/20
See application file for complete search history.

(56) References Cited

U.S. PATENT DOCUMENTS

| | | | |
|---|---|---|---|
| 2,994,642 | A | 8/1961 | Bossard |
| 3,393,678 | A | 7/1968 | Pacini |
| 3,803,308 | A | 4/1974 | Zipper |
| 3,814,809 | A | 6/1974 | Gordon |

(Continued)

FOREIGN PATENT DOCUMENTS

| | | |
|---|---|---|
| AU | 040296/72 | 9/1973 |
| AU | 2020201265 | 9/2021 |

(Continued)

OTHER PUBLICATIONS

US 11,052,109 B2, 07/2021, Abbott et al. (withdrawn)
US 11,229,598 B2, 01/2022, Abbott et al. (withdrawn)
US 11,266,597 B2, 03/2022, Abbott et al. (withdrawn)
Glaser et al. Pilot Study: Absorption and Efficacy of Multiple Hormones Delivered in a Single Cream Applied to the Mucous Membranes of the Labia and Vagina. Apr. 29, 2008. Gynecologic and Obstetric Investigation. vol. 66. pp. 111-118. DOI: 10.1159/000128599. (Year: 2008).\*
National Research Council (US) Committee on Copper in Drinking Water. Washington (DC): National Academies Press (US); 2000. (Year: 2000).\*
"10 Homemade Gargles That Heal", Reader's Digest of Canada, www.readersdigest.ca/health/conditions/gaggle-gargles/, Jan. 4, 2008 (3 pages).

(Continued)

*Primary Examiner* — Tracy Liu
(74) *Attorney, Agent, or Firm* — Wilmer Cutler Pickering Hale and Dorr LLP

(57) ABSTRACT

Provided herein are topical formulations containing copper ions and methods of treating radiation dermatitis, damage caused by radiation therapy, or other radiation-induced damage conditions in various areas of the body using such formulations. Methods of treating radiation dermatitis using topical copper ion treatments are provided. A topical treatment in its basic form comprises a biocompatible copper ion solution or suspension obtained by leaching of the copper ions from copper metal. The copper ion solution or suspension is combined with various carriers to form the copper ion treatment including creams, gels, lotions, foams, pastes, tampons, solutions, suppositories, body wipes, wound dressings, skin patches, and suture material. Methods of making the copper ion solution or suspension from solid copper metal in a biocompatible solution are also provided.

30 Claims, 11 Drawing Sheets

(56) References Cited

U.S. PATENT DOCUMENTS

| | | | |
|---|---|---|---|
| 3,930,834 A * | 1/1976 | Schulteis | C07F 1/005 |
| | | | 504/152 |
| 3,934,580 A | 1/1976 | Cournut | |
| 4,039,406 A | 8/1977 | Stanley et al. | |
| 4,136,172 A | 1/1979 | Walliczek | |
| 4,242,192 A | 12/1980 | Dunning, Jr. et al. | |
| 4,246,896 A | 1/1981 | Horne, Jr. et al. | |
| 4,294,894 A | 10/1981 | Vellucci | |
| 4,332,791 A | 6/1982 | Raaf et al. | |
| 4,391,270 A | 7/1983 | Uragami | |
| 4,407,786 A | 10/1983 | Drake et al. | |
| 4,457,909 A | 7/1984 | Tames | |
| 4,618,489 A | 10/1986 | Pollock et al. | |
| 4,642,230 A | 2/1987 | Whitehead et al. | |
| 4,661,101 A | 4/1987 | Sustmann | |
| 4,675,014 A | 6/1987 | Sustmann et al. | |
| 4,680,309 A | 7/1987 | Maurer | |
| 4,795,628 A | 1/1989 | Afseth | |
| 4,959,216 A | 9/1990 | Daunter | |
| 5,037,634 A | 8/1991 | Williams et al. | |
| 5,063,065 A | 11/1991 | Bazterrica et al. | |
| 5,164,367 A | 11/1992 | Pickart | |
| 5,211,940 A | 5/1993 | Ishiguro et al. | |
| 5,389,360 A | 2/1995 | Mobley et al. | |
| 5,415,866 A | 5/1995 | Zook | |
| 5,425,862 A | 6/1995 | Hartmann et al. | |
| 5,456,602 A | 10/1995 | Sakuma | |
| 5,458,746 A * | 10/1995 | Burgess | C22B 15/0067 |
| | | | 423/604 |
| 5,631,017 A | 5/1997 | Sharpe et al. | |
| 5,654,341 A * | 8/1997 | Struewing | A61K 8/361 |
| | | | 514/762 |
| 5,798,116 A | 8/1998 | Brown | |
| 5,981,475 A | 11/1999 | Reynolds | |
| 6,022,545 A | 2/2000 | Schmittmann et al. | |
| 6,042,848 A | 3/2000 | Lawyer et al. | |
| 6,087,549 A | 7/2000 | Flick | |
| 6,123,925 A | 9/2000 | Barry et al. | |
| 6,153,210 A | 11/2000 | Roberts et al. | |
| 6,231,889 B1 | 5/2001 | Richardson et al. | |
| 6,294,186 B1 | 9/2001 | Beerse et al. | |
| 6,296,881 B1 | 10/2001 | Hata et al. | |
| 6,319,391 B1 | 11/2001 | Holderness et al. | |
| 6,383,352 B1 | 5/2002 | Shyu et al. | |
| 6,787,160 B2 * | 9/2004 | Shacknai | A61K 8/26 |
| | | | 424/724 |
| 7,005,556 B1 | 2/2006 | Becker et al. | |
| 7,087,249 B2 | 8/2006 | Burrell et al. | |
| 7,252,839 B2 | 8/2007 | Hallinen et al. | |
| 7,604,819 B2 | 10/2009 | Huey et al. | |
| 7,776,915 B2 | 8/2010 | Morariu | |
| 7,857,961 B2 | 12/2010 | Hayashi et al. | |
| 8,118,028 B2 | 2/2012 | Karpati | |
| 8,135,466 B2 | 3/2012 | Fuller et al. | |
| 8,182,800 B2 | 5/2012 | MacDonald | |
| 10,398,733 B2 | 9/2019 | Abbott et al. | |
| 11,000,545 B2 | 5/2021 | Abbott et al. | |
| 11,007,143 B2 | 5/2021 | Abbott et al. | |
| 11,083,750 B2 | 8/2021 | Abbott et al. | |
| 11,193,184 B2 | 12/2021 | Abbott et al. | |
| 11,253,544 B2 | 2/2022 | Abbott et al. | |
| 11,298,316 B2 | 4/2022 | Abbott | |
| 11,318,089 B2 | 5/2022 | Abbott et al. | |
| 11,459,638 B2 | 10/2022 | Abbott et al. | |
| 11,717,535 B2 | 8/2023 | Abbott | |
| 11,857,514 B2 | 1/2024 | Abbott | |
| 2002/0114767 A1 | 8/2002 | Rolla | |
| 2002/0136758 A1 | 9/2002 | Jehan | |
| 2003/0099718 A1 | 5/2003 | Burrell et al. | |
| 2003/0163149 A1 | 8/2003 | Heisinger | |
| 2003/0166510 A1 | 9/2003 | Pickart | |
| 2004/0120908 A1 * | 6/2004 | Cohen | A61K 8/26 |
| | | | 424/63 |
| 2004/0171519 A1 | 9/2004 | DiSpirito et al. | |
| 2004/0182694 A1 | 9/2004 | Ulderico | |
| 2004/0234457 A1 | 11/2004 | Rennie | |
| 2004/0254097 A1 | 12/2004 | Patt | |
| 2005/0031707 A1 | 2/2005 | Schmidt et al. | |
| 2005/0048007 A1 | 3/2005 | Ruggles | |
| 2005/0123620 A1 | 6/2005 | Chiou | |
| 2005/0169852 A1 | 8/2005 | Roberge et al. | |
| 2005/0226945 A1 * | 10/2005 | Ruwart | A61K 31/355 |
| | | | 514/547 |
| 2006/0122095 A1 | 6/2006 | Delvin et al. | |
| 2006/0216258 A1 | 9/2006 | Singleton et al. | |
| 2006/0222622 A1 * | 10/2006 | Faure | A61K 38/38 |
| | | | 424/78.27 |
| 2006/0253078 A1 | 11/2006 | Wu et al. | |
| 2007/0014839 A1 | 1/2007 | Bracht | |
| 2007/0053849 A1 | 3/2007 | Doyle et al. | |
| 2007/0167971 A1 | 7/2007 | Huey et al. | |
| 2007/0187327 A1 | 8/2007 | George et al. | |
| 2007/0190175 A1 | 8/2007 | Cummins et al. | |
| 2007/0243263 A1 | 10/2007 | Trogolo | |
| 2007/0275021 A1 | 11/2007 | Lee et al. | |
| 2007/0275073 A1 | 11/2007 | Huey et al. | |
| 2007/0276308 A1 | 11/2007 | Huey et al. | |
| 2008/0029915 A1 | 2/2008 | Waldron | |
| 2008/0032119 A1 | 2/2008 | Feldhahn et al. | |
| 2008/0081077 A1 * | 4/2008 | Faryniarz | A61K 45/06 |
| | | | 530/356 |
| 2008/0112988 A1 | 5/2008 | Frank et al. | |
| 2008/0125686 A1 | 5/2008 | Lo | |
| 2008/0193427 A1 | 8/2008 | Kaesler et al. | |
| 2008/0195033 A1 | 8/2008 | Eagleson et al. | |
| 2008/0274065 A1 | 11/2008 | Robinson et al. | |
| 2008/0286180 A1 | 11/2008 | Jones | |
| 2008/0286212 A1 | 11/2008 | Cooley | |
| 2008/0295843 A1 | 12/2008 | Haas | |
| 2008/0299155 A1 | 12/2008 | McCook et al. | |
| 2008/0311165 A1 | 12/2008 | Gabbay | |
| 2008/0311167 A1 * | 12/2008 | Oronsky | A61P 11/00 |
| | | | 514/552 |
| 2008/0311218 A1 | 12/2008 | Oronsky et al. | |
| 2008/0312583 A1 | 12/2008 | Oronsky et al. | |
| 2008/0317836 A1 | 12/2008 | Dorogi et al. | |
| 2009/0004294 A1 | 1/2009 | Margulies et al. | |
| 2009/0018213 A1 | 1/2009 | Snyder et al. | |
| 2009/0026083 A1 | 1/2009 | Shinji et al. | |
| 2009/0148540 A1 | 6/2009 | Martin et al. | |
| 2009/0163551 A1 * | 6/2009 | Earnest | A61P 21/04 |
| | | | 514/338 |
| 2009/0186071 A1 | 7/2009 | Huey et al. | |
| 2009/0246292 A1 | 10/2009 | Seville et al. | |
| 2009/0287131 A1 | 11/2009 | Neron et al. | |
| 2009/0304813 A1 | 12/2009 | Hickok | |
| 2009/0311305 A1 | 12/2009 | Abbott et al. | |
| 2010/0003198 A1 | 1/2010 | Stolmeier et al. | |
| 2010/0015898 A1 | 1/2010 | An et al. | |
| 2010/0055138 A1 | 3/2010 | Margulies et al. | |
| 2010/0068161 A1 * | 3/2010 | Todary Michael | A61K 8/27 |
| | | | 424/59 |
| 2010/0068297 A1 | 3/2010 | Naughton | |
| 2010/0100188 A1 | 4/2010 | Fuller et al. | |
| 2010/0158989 A1 | 6/2010 | Mentkow et al. | |
| 2010/0228174 A1 | 9/2010 | Huey et al. | |
| 2010/0233248 A1 | 9/2010 | Huey et al. | |
| 2010/0307503 A1 | 12/2010 | Iwamoto et al. | |
| 2011/0064826 A1 | 3/2011 | Spurge | |
| 2011/0086088 A1 * | 4/2011 | Berry | A61P 17/00 |
| | | | 424/450 |
| 2011/0195108 A1 | 8/2011 | Fujimori et al. | |
| 2012/0063262 A1 | 3/2012 | Imran | |
| 2012/0070476 A1 | 3/2012 | Moench | |
| 2012/0071807 A1 | 3/2012 | McClure, Jr. | |
| 2012/0071858 A1 | 3/2012 | Abbott et al. | |
| 2012/0089068 A1 | 4/2012 | McClure, Jr. | |
| 2013/0095184 A1 | 4/2013 | Lyczak et al. | |
| 2013/0108670 A1 * | 5/2013 | Lynch | A61K 38/1858 |
| | | | 514/8.1 |
| 2013/0123716 A1 | 5/2013 | Abbott et al. | |
| 2013/0226061 A1 | 8/2013 | Dickson | |

(56) References Cited

U.S. PATENT DOCUMENTS

| | | |
|---|---|---|
| 2013/0309219 A1 | 11/2013 | Ratner |
| 2014/0005116 A1 | 1/2014 | Obayan et al. |
| 2014/0178313 A1 | 6/2014 | Okumura et al. |
| 2014/0221948 A1* | 8/2014 | Riesinger ............... A61L 15/60 604/319 |
| 2014/0271495 A1 | 9/2014 | Abbott et al. |
| 2014/0271797 A1 | 9/2014 | Abbott et al. |
| 2014/0271798 A1 | 9/2014 | Abbott et al. |
| 2014/0271919 A1 | 9/2014 | Abbott et al. |
| 2016/0008272 A1 | 1/2016 | Abbott et al. |
| 2017/0000823 A1 | 1/2017 | Abbott et al. |
| 2017/0101699 A1 | 4/2017 | Moskovchenko et al. |
| 2018/0071206 A1 | 3/2018 | Abbott et al. |
| 2018/0133250 A1 | 5/2018 | Abbott et al. |
| 2019/0343732 A1* | 11/2019 | Mao ..................... A61K 8/0204 |
| 2019/0343876 A1 | 11/2019 | Abbott et al. |
| 2020/0270723 A1 | 8/2020 | Abbott et al. |
| 2020/0281972 A1 | 9/2020 | Abbott et al. |
| 2021/0220397 A1 | 7/2021 | Abbott et al. |
| 2021/0220398 A1 | 7/2021 | Abbott et al. |
| 2021/0220399 A1 | 7/2021 | Abbott et al. |
| 2021/0228476 A1 | 7/2021 | Abbott et al. |
| 2022/0226235 A1 | 7/2022 | Abbott et al. |
| 2023/0330137 A1 | 10/2023 | Abbott et al. |

FOREIGN PATENT DOCUMENTS

| | | | |
|---|---|---|---|
| CA | 2478137 A1 | 2/2006 | |
| CA | 2912628 | 9/2014 | |
| CA | 3130099 | 8/2020 | |
| CN | 101203232 A | 6/2008 | |
| CN | 101534823 A | 9/2009 | |
| EP | 0115130 B1 | 1/1987 | |
| EP | 1236461 A1 | 9/2002 | |
| EP | 1627641 A1 | 2/2006 | |
| EP | 3003046 B1 | 4/2016 | |
| EP | 2762125 B1 | 8/2016 | |
| FR | 2751544 A1 | 1/1998 | |
| GB | 521215 A | 5/1940 | |
| GB | 1333906 A | 10/1973 | |
| GB | 1493750 A | 11/1977 | |
| GB | 2449893 A | 12/2008 | |
| JP | 3075995 U | 3/2001 | |
| JP | 2003212765 A | 7/2003 | |
| JP | 2010-265519 A | 11/2010 | |
| RU | 2051154 C1 | 12/1995 | |
| RU | 2155047 C1 | 8/2000 | |
| SU | 1538101 | 1/1990 | |
| WO | WO-9215329 A1 | 9/1992 | |
| WO | WO-9958095 A2 | 11/1999 | |
| WO | WO-2001026665 A1 | 4/2001 | |
| WO | WO-0239963 A1 | 5/2002 | |
| WO | WO-0241862 A1 | 5/2002 | |
| WO | WO-02096202 A1 | 12/2002 | |
| WO | WO-2004073758 A1 | 9/2004 | |
| WO | WO-2005072691 A1 | 8/2005 | |
| WO | WO-2006096937 A1 | 9/2006 | |
| WO | WO-2008037262 A1 * | 4/2008 | ............ A61K 33/26 |
| WO | WO-2009042402 A2 * | 4/2009 | ........... A61K 31/192 |
| WO | WO-2009088270 | 7/2009 | |
| WO | WO-2011069184 A1 | 6/2011 | |
| WO | WO-2012063262 A2 | 5/2012 | |
| WO | WO-2014150716 A1 | 9/2014 | |
| WO | WO-2014150719 A1 | 9/2014 | |
| WO | WO-2014151350 | 9/2014 | |
| WO | WO-2018052995 | 3/2018 | |
| WO | WO-2020171994 | 8/2020 | |
| WO | WO-2021222230 | 11/2021 | |
| WO | WO-2021236231 | 11/2021 | |

OTHER PUBLICATIONS

"Buffer Reference Center", https://www.sigmaaldrich.com/life-science/core-bioreagents/biological-buffers/learning-center/buffer-reference-center.html, Oct. 26, 2008 (6 pages).

Azo Materials, "Medical Applications of Stainless Steel 304 (UNS S30400)", azom.com/Articles.aspx?=6641, Aug. 30, 2012 (3 pages).

Blanc, C. et al., "Galvanic coupling between copper and aluminium in a thin-layer cell", Corrosion Science, 52(3):991-995, 2010 (6 Pages).

European Extended Search Report issued in EP20185469.2, dated Oct. 9, 2020 (10 pages).

Fenelon, A.M. et al., "The electrochemical synthesis of polypyrrole at a copper electrode: corrosion protection properties", Electrochimica Acta, 47:4467-4476, 2002 (10 pages).

Google Search "Copper Salt for Sore Throat 'Coronavirus'", dated Aug. 24, 2020 (2 pages).

Gray, L.W. et al., "Urinary Copper Elevation in a Mouse Model of Wilson's Disease Is a Regulated Process to Specifically Decrease the Hepatic Copper Load", PLoS One, 7(6):e38327, Jun. 22, 2012 (11 pages).

Read, A.J., "Dissolution of Copper in Weakly Acidic Solutions", The Journal of Physical Chemistry, 76(24):3656-3663, 1972 (8 pages).

Zwirner, E., "5 Advantages of Vertical Storage Tanks", https://www.zwirnerequipment.com/blog/5-advantages-vertical-storage-tanks/, Oct. 20, 2014 (2 pages).

"Assessment of the Safety and Efficacy of 3VM1001 Cream for Treatment of Chronic Pain Caused by Knee Osteoarthritis", ClinicalTrials.gov, https://clinicaltrials.gov/ct2/history/NCT02332148?V_3, dated Aug. 19, 2015 (6 pages).

"Copper Sulfate", extract from Extoxnet: Extension Toxicology Network, <http://pmep.cce.cornell.edu/profiles/extoxnet/carbaryl-dicrotophos/copper-sulfate-ext.html>, May 1994 (2 pages).

"Copper Sulphate's Role in Agriculture", Excerpt from PAN Pesticides Database—Chemicals (1 page).

"Dangers of Copper Compounds (Sulfate, etc.)", Pubchem.ncbi.nlm.nih.gov/compound/Copper_sulfate#section=Top, 2007 (17 pages).

"Lowering Infection Rates in Hospitals and Healthcare Facilities—The Role of Copper Alloys in Battling Infectious Organisms", Copper, BioHealth Partnership Publication, Edition 1, Mar. 2007, 26 pages.

"New Molecular Test Available to Diagnose Trichomonas Vaginalis in Asymptomatic and Symptomatic Females", PR Newswire, Oct. 18, 2012, 3 pages.

"Visual Analogue Scale", https://web.archive.org/web/20150804080655/https://www.physio-pedia.com/Visual_Analogue_Scale, Aug. 4, 2015, accessed Dec. 13, 2017 (6 pages).

"WOMAC Osteoarthritis Index," https://web.archive.org/web/20150907191904/https://www.physio-pedia.com/WOMAC_Osteoarthritis_Index, Sep. 7, 2015, accessed Dec. 13, 2017 (4 pages).

Amazon.com search for "Mouthwash", https://www.amazon.com/s/ref=sr_nr_n_0?fst=p90x%3A1%2Cas%3Aoff&rh=n%3A3760911%2Cn%3A100799992011%2Cn%3A3778161%2Ck%3Amouthwash&keywords=mouthwash&ie=UTF8&qid=1502940655&rnid=11055981, dated Aug. 16, 2017 (11 pages).

Anthoni, F. "The Chemical Composition of Seawater", http://www.seafriends.org.nz/oceano/seawater.htm, downloaded Jul. 28, 2016 (10 pages).

ASTM International, Designation: D1688-12, "Standard Test Methods for Copper in Water", dated 2012, accessed Oct. 24, 2018 (10 pages).

Bhunya, et al., "Genotoxicity of an Inorganic Pesticide, Copper Sulphate in Mouse in vivo Test System", Cytologia, 52:801-808, 1987 (8 pages).

Blakley, B.R. "Overview of Copper Poisoning", Merck Manual: Veterinary Manual, https://www.merckvetmanual.com/toxicology/copper-poisoning/overview-of-copper-poisoning, 2018 (3 pages).

Borkow, G. et al., "Copper as a Biocidal Tool", Current Medicinal Chemistry, 12:2163-2175 (2005) (13 pages).

Cao, "Man Sperm Self Report", Harbin Publishing House, p. 27, Mar. 2012 (2 pages)—with English Translation.

CDA Research Group, Inc., "Assessment of the Safety and Efficacy of 3VM1001 Cream for Treatment of Chronic Pain Caused by Knee Osteoarthritis", U.S. National Library of Medicine, Clinical Trial NCT02332148, https://clinicaltrials.gov/ct2/show/NCT02332148, Aug. 21, 2015, accessed Dec. 12, 2017 (5 pages).

(56) References Cited

OTHER PUBLICATIONS

Centers for Disease Control, "CDC No Longer Recommends Oral Drug for Gonorrhea Treatment", Press Release, Aug. 9, 2012, 1 page.
Centers for Disease Control. "Pelvic Inflammatory Disease (PID)", CDC Fact Sheet, Dec. 12, 2012, 6 pages.
Collins, Reflections of Dentifrice Ingredients, Benefits and Recommendations: A Peer-Reviewed Publication, www.ineedce.com, accessed https://www.dentalacademyofce.com/courses/2086/pdf/1103cei_dentifrices_web.pdf, Oct. 2009 (11 pages).
Copper Gluconate, except from Wikipedia, https://en.wikipedia.org/wiki/Copper_gluconate, Mar. 29, 2017 (1 page).
Copper Glycinate Product Data Sheet, https://www.lookchem.com/Copper-glycinate/, dated 2008, accessed Aug. 30, 2018 (2 pages).
Database WPI, Week 199640, Thompson Scientific, London GB, AN 1996-400647, XP002765918, 1996 (2 pages).
Database WPI, Week 200375, Thompson Scientific, AN 2003-793474, XP002767346, 2003 (2 pages).
Dispose—definition, https://www.merriam-webster.com/dictionary/dispose, downloaded Jun. 24, 2018 (1 page).
Dragani, R. "Does Salt Change the pH of Water?", https://sciencing.com/does-salt-change-ph-water-4577912.html., downloaded Dec. 31, 2019, Apr. 19, 2018 (3 pages).
Edematous—Definition from The Medical Dictionary of the Free Dictionary Online, https://medical-dictionary.thefreedictionary.com/edematous, accessed Mar. 7, 2018 (7 pages).
European Extended Search Report issued in EP14767396.6, dated Feb. 9, 2017 (10 pages).
European Extended Search Report issued in EP14768757.8, dated Dec. 6, 2016 (9 pages).
European Extended Search Report issued in EP14768896.4, dated Feb. 27, 2017 (8 pages).
Extended European Search Report issued in EP14767738.9, dated Jan. 2, 2017 (8 pages).
Faltermeier, R. B., "The Evaluation of Corrosion Inhibitors for Application to Copper and Copper Alloy Archaeological Artefacts", Thesis Submitted for the Degree of Doctor of Philosophy in the Faculty of Science of the University of London, Department of Conservation and Museum Studies, Institute of Archaeology, University College London, University of London, Jul. 1995 (332 pages).
Gerasimov, V. V. et al., "Effect of Temperature on the Rate of Corrosion of Metals", Russian Chemical Bulleting, pp. 1192-1197, Oct. 6, 1957 (6 pages).
Higdon, J. et al., "Copper", Linus Pauling Institute, Oregon State University, Apr. 2003, 8 pages.
International Search Report and Written Opinion issued by U.S. Patent and Trademark Office as International Searching Authority, in International Application No. PCT/US17/51356, Jan. 18, 2018 (11 pages).
Ion, Wikipedia, https://en.wikipedia.org/wiki/Ion, accessed Aug. 30, 2018 (11 pages).
Kirkpatrick, K., "Does saltwater work as mouthwash?", http://health.howstuffworks.com/wellness/oral-care/products/saltwater-as-mouthwash.htm, available online Sep. 18, 2011, accessed Mar. 4, 2019 (6 pages).
Lindeburg, M.R., Chemical Engineering Reference Manual for the PE Exam, 7th Edition, Professional Publications, Inc., Belmont, CA, 2013, p. 20-10 (3 pages).
Malik, R. "Warm Saline Rinses", http://www.nature.com/articles/sj.bdj.2009.1093.pdf, accessed Dec. 31, 2019, Br. Dental J., 207(11):520, 2009 (2 page).
Marques, M.R.C. et al., "Simulated Biological Fluids with Possible Application in Dissolution Testing", Dissolution Technologies, 18(3):15-28, Aug. 2011 (14 pages).
Metikoš-Hukovi, M. et al., "Copper Corrosion at Various pH Values with and without the Inhibitor", Journal of Applied Electrochemistry, 30:617-624, 2000 (8 pages).

Michels, et al., "Copper Alloys for Human Infectious Disease Control", presented at Materials Science Technology Conference, Sep. 25-28, 2005, Pittsburgh, PA, Copper for the 21st Century Symposium, 11 pages.
Nkonzo, N., "Antimicrobial Copper", International Copper Association, Copper Development Association, May 5, 2010, 6 pages.
Owen, D.H. et al., "A Vaginal Fluid Simulant", Contraception, 59(2):91-95, Feb. 1999 (5 pages).
Perrie, Y. et al., "Chapter 1: Controlling Drug Delivery", FASTtrack: Pharmaceutics—Drug Delivery and Targeting, Second Edition, Sample Chapter, 14, Jun. 2012 (26 pages).
Ramachandran, S. et al., "Gluconic Acid: Properties, Applications and Microbial Production", Food Technol. Biotechnol., 44(2):185-195, 2006 (11 pages).
Roldan, S, et al., "Biofilms and the tongue: therapeutical approaches for the control of halitosis", Clin. Oral Invest., 7:189-197, 2003 (9 pages).
Rosenhein, L.D., "The Household Chemistry of Cleaning Pennies", Applications and Analogies, Journal of Chemical Education, 78(4):513-515, Apr. 2001 (3 pages).
Sawyer, D.T., "Metal-Gluconate Complexes", Chem. Rev., 64(6):633-643, 1964 (11 pages).
Solioz, "Dry Copper Kills Bacteria on Contact", Science Daily, Feb. 22, 2011, 4 pages.
Stein, R., "Gonorrhea Evades Antibiotics, Leaving Only One Drug to Treat Disease", www.npr.org/blogs/health, Aug. 10, 2012, 5 pages.
VersaBase Cream, Product Information Document, from PCCA, https://pccarx.com/Products/ProductCatalog?pid=30-3641, accessed Dec. 31, 2019 (4 pages).
Wang, et al., "Family Planning Technology", Shanghai Science and Technology Press, p. 334, Dec. 31, 1997 (2 pages)—English Excerpt.
Wikipedia, "Acetic acid", https://en.wikipedia.org/wiki/Acetic_acid, Oct. 14, 2019 (19 pages).
Wikipedia, "Buffer Solution", Wikipedia, the Free Encyclopedia, https://en.wikipedia.org/wiki/Buffer_Solution, accessed Apr. 7, 2017 (8 pages).
Wikipedia, "Copper(I) chloride", https://en.wikipedia.org/wiki/Copper(I)_chloride, accessed Oct. 13, 2019 (8 pages).
Wikipedia, "Salt (chemistry)", https://en.wikipedia.org/wiki/Salt_(chemistry), accessed Oct. 14, 2019 (6 pages).
Wikipedia, "Suspension (chemistry)", https://en.wikipedia.org/wiki/Suspension_(chemistry), accessed Oct. 13, 2019 (3 pages).
Zatcoff, R.C. et al., "Treatment of tinea pedis with socks containing copper-oxide impregnated fibers", The Foot, 18:136-141 (2008) (6 pages).
European Partial Supplementary Search Report issued in EP17851454.3, dated Apr. 6, 2020 (14 pages).
Khaled, K.F., "Studies of the corrosion inhibition of copper in sodium chloride solutions using chemical and electrochemical measurements", Materials Chemistry and Physics, 125:427-433, 2011 (7 pages).
Saxer, U P et al., "New Studies on Estimated and Actual Toothbrushing Times and Dentifrice Use", J. Clin. Dent., 9(2):49-51, 1998 (1 page)—Abstract Only.
Shackel, N.A. et al., "Copper-salicylate gel for pain relief in osteoarthritis: a randomised controlled trial", MJA, 167:134-136, Aug. 4, 1997 (3 pages).
Tamba, B.I. et al., "Common Trace Elements Alleviate Pain in an Experimental Mouse Model", Journal of Neuroscience Research, 91:554-561, 2013 (8 pages).
Yassin, N. et al., "Effect of a topical copper indomethacin gel on inflammatory parameters in a rat model of osteoarthritis", Drug Design, Development and Therapy, 9:1491-1498, 2015 (8 pages).
"Difference Between 304 vs 316 Stainless Steel", Eagle Stainless Tube & Fabrication, Inc., https://eagletube.com/about-us/news/304-vs-316-stainless-steel, Jun. 21, 2018 (2 pages).
Duguid, R., "Copper-inhibition of the growth of oral streptococci and actinomyces", Biomaterials, 4:225-227, Jul. 1983 (3 pages).
European Extended Search Report, issued in European Patent Application No. 17851454.3, dated Jul. 10, 2020 (15 pages).

(56) References Cited

OTHER PUBLICATIONS

International Search Report and Written Opinion issued by the U.S. Patent and Trademark Office as International Searching Authority, issued in International Application No. PCT/US2020/17454, dated Jun. 23, 2020 (12 pages).
Maltz, M. et al., "Effect of copper fluoride and copper sulfate on dental plaque, Streptococcus mutans and caries in hamsters", Scand. J. Dent. Res., 96:390-392, Oct. 1, 1988 (3 pages).
Moore, R.L. et al., "Evaluating the Anti-Plaque Capabilities of a Copper-Containing Prophylaxis Paste", J. Periodontal., 60(2):78-80, Feb. 1989 (3 pages).
Mulligan, A.M. et al., "The effect of increasing copper content in phosphate-based glasses on biofilms of Streptococcus sanguis", Biomaterials, 24:1797-1807, 2003 (11 pages).
"Antimicrobial Copper FAQs", CDA Publication 201, Copper Development Association, Hemel Hempstead, United Kingdom, 2010 (8 pages).
Beigel, J.H. et al., "Remdesivir for the Treatment of Covid-19—Final Report", The New England Journal of Medicine, 383(19):1813-1826, published online Oct. 9, 2020 (14 pages).
CDA Research Group, Inc., "A Double-Blind, Placebo-Controlled, Crossover Study to Evaluate the Efficacy and Tolerability of 3VM1001 Cream for the Treatment of Pain Associated With Post-Herpetic Neuralgia: A Proof of Concept Study", Identifier NCT03421613, published on clinicaltrials.gov <URL: https://www.clinicaltrials.gov/ct2/show/NCT03421613>, published Jul. 10, 2018 (8 pages).
CDA Research Group, Inc., "A Double-blind, Placebo-controlled, Randomized Study to Assess the Safety and Efficacy of 3VM1001 Cream for the Treatment of Chronic Pain Caused by Osteoarthritis of the Knee: A Proof of Concept Study", Identifier: NCT02332148, Published on ClinicalTrials.Gov, <URL: https://clinicaltrials.gov/ct2/show/NCT02332148>, Published Aug. 21, 2015 according to ClinicalTrials.Gov (6 pages).
CDA Research Group, Inc., "A Double-Blind, Placebo-Controlled, Randomized Study to Evaluate the Safety and Efficacy of 3VM1001 Cream for the Treatment of Chronic Pain Caused by Osteoarthritis of the Knee: A Dose Ranging Study", Identifier: NCT03142178 published on clinicaltrials.gov <URL: https://www.clinicaltrials.gov/ct2/show/ NCT03142178 >, published Jul. 6, 2018 according to ClinicalTrials.Gov (9 pages).
De Rauglaudre, G. et al., "Tolerance of the association sucralfate / Cu—Zn salts in radiation dermatitis", Annales de dermatologie, 1:11-15 (2008)—English Abstract (5 pages).
Robinson, J., "No improvement in mortality rates for COVID-19 patients treated with remdesivir", the Pharmaceutical Journal, DOI:10.1211/PJ.2020.20208045, published online Jun. 8, 2020 (3 pages).
Bianchetti, M. G., et al., "Body fluids and salt metabolism—Part I", Italian Journal of Pediatrics, 35:36, 2009 (6 pages).
Al-Kharafi, et al., "Selective dissolution of brass in salt water", Journal of Applied Electrochemistry, 34:47-53, 2004 (7 pages).
Bauer, "Understanding radiation dermatitis", American Nurse Today, 11(1):13-15, Jan. 2016 (3 pages).
Bauer, "Understanding radiation dermatitis", URL<http://old.woundcareadvisor.com/understanding-radiation-dermatitis/>, Wound Care Advisor, vol. 5, No. 3, May/Jun. 2016 (6 pages).
Ben-Hur, et al., "Phosphorus Burns: The Antidote: A New Approach", British Journal of Plastic Surgery, 25:245-249, 1972 (5 pages).
Biocompatible, definition from Cambridge Dictionary, URL <https://dictionary.cambridge.org/us/dictionary/english/biocompatible>, accessed Oct. 26, 2020 (6 pages).
Cancer Facts & Figures 2016, American Cancer Society, URL <https://www.cancer.org/research/cancer-facts-statistics/all-cancer-facts-figures/cancer-facts-figures-2016.html>, 2016 (72 pages).
Cortes, et al., "The use of copper to help prevent transmission of SARS-coronavirus and influenza viruses. A general review", Diagnostic Microbiology and Infectious Disease, 98:115176, available online Aug. 15, 2020 (5 pages).
Google Search, "copper in sea salt", URL <https://www.google.com/search?q=copper+in+sea+salt&ei=TRrWYJyaCemr5NoPvlmPiA . . . >, accessed Jun. 25, 2021 (2 pages).
Google Search, "Copper phosphate buffered saline", URL: <https://scholar.google.com/scholar?hl=en&as_sdt=0%2C47&q=copper=+phosphate+buffered . . . >, accessed Aug. 5, 2021 (2 pages).
Google Search, "dead sea salt and acetate buffer mouthwash", URL <https://www.google.com/search?q=dead+sea+salt+and+acetate+buffer+mouthwash&ei=d . . . >, accessed Jun. 25, 2021 (2 pages).
Google Search, "mouthwash dead sea salt and acetate buffer", URL <https://google.com/search?q=mouthwash+dead+sea+salt+and+acetate+buffer&tbm=. . . >, accessed Jun. 25, 2021 (2 pages).
International Search Report and Written Opinion issued by the U.S. Patent and Trademark Office as International Searching Authority, in International Application No. PCT/US21/24555, dated Jul. 8, 2021 (9 pages).
Iqbal, K. et al., "Role of Different Ingredients of Tooth Pastes and Mouthwashes in Oral Health", Journal of the Pakistan Dental Association, 20(03):163-170, Jul.-Sep. 2011 (8 pages).
Pramanik, et al., "A novel study of antibacterial activity of copper iodide nanoparticle mediated by DNA and membrane damage", Colloids and Surfaces B: Biointerfaces, 96:50-55, published online Apr. 5, 2012 (6 pages).
Wikipedia, "Saline (Medicine)", URL <https://en.wikipedia.org/wiki/Saline_(medicine)>, accessed Jul. 21, 2021 (9 pages).
Wong, R. K. S. et al., "Clinical practice guidelines for the prevention and treatment of acute and late radiation reactions from the MASCC Skin Toxicity Study Group", Support Care Cancer, DOI 10.1007/s00520-013-1896-2, published online Aug. 14, 2013 (16 pages).
Kole, A., et al., "Acute radiation dermatitis in breast cancer patients: challenges and solutions", Breast Cancer—Targets and Therapy, 9:313-323, May 5, 2017 (11 pages).
Leventhal, J., et al., "Radiation Dermatitis: Recognition, Prevention, and Management", Oncology (Williston Park), 31(12): Dec. 15, 2017 (10 pages).
Physiological Saline, definition from APA Dictionary of Psychology, <URL: https://dictionary.apa.org/physiological-saline[Oct. 5, 2021 11:47:23 AM], 1 page.
Ryan, J., "Ionizing Radiation: The Good, the Bad, and the Ugly", Author Manuscript published in final edited form as J Invest Dermatol., 132(3 0 2):985-993, Mar. 2012 (16 pages).
Ryan, J., et al., "Curcumin for Radiation Dermatitis: A Randomized, Double-Blind, Placebo-Controlled Clinical Trial of Thirty Breast Cancer Patients", Author Manuscript published in final edited form as Radiat Res., 180(1):34-43, Jul. 2013 (20 pages).
Sims, "'Breast Cancer Isn't Sexy': Woman Shares Post-Radiation Images to Show Reality of Disease", The Independent, <URL: https://www.independent.co.uk/life-style/health-and-families/health-news/breast-cancer-isn-t-sexy-woman-shares-postradiation-images-to-show-reality-of-disease-a6709516.html>, Oct. 26, 2015 (4 pages).
Williams, M., et al., "Phase III double-blind evaluation of an aloe vera gel as a prophylactic agent for radiation-induced skin toxicity", I. J. Radiation Oncology Biology Physics, 36(2):345-349, Sep. 1, 1996 (5 pages).
Khan, "Taanbey-ka-Kushta", Traditional Knowledge Resource, Traditional Knowledge and Digital Library, Khazaain-al-Advia, vol. II (20th Century Ghani AD), Nadeem Yunus Printer, Sheikh Mohd Basheer & Sons, Lahore, pp. 155-156, 1911 (4 pages).
Madanapala, "Tamra Guna", Traditional Knowledge Resource, Traditional Knowledge and Digital Library, Translated by Rama Prasad, Khemraj Shri Krishnadas, Prakashan, Bombay, India, p. 98, 1998 (4 pages).
Shaligram, et al., "Toxicity of copper salts is dependent on solubility profile and cell type tested", Toxicology in Vitro, 27(2):844-851, Mar. 2013, available online Dec. 31, 2012 (9 pages).
"Copper(II) Sulfate, Pentahydrate", ICSC 1416, CAS#: 7758-99-8, EC No. 231-847-6, International Labour Organization, World Health Organization, www.ilo.org/dyn/icsc/showcard.display?p_lang=en&p_card_id=1416&p_version=2, Oct. 2001 (2 pages).
"VersaBase Cream, PCCA (RX): Ingredients and Reviews", https://www.skinsafeproducts.com/versabase-cream-rx-pcca, accessed Jun. 3, 2022 (5 pages).

(56) References Cited

OTHER PUBLICATIONS

Aaseth, J. et al., "Chapter 10: Copper (excerpt)", from Handbook on the Toxicology of Metals, Second Edition, vol. II: Specific Metals, Freiberg, et al., Eds., Elsevier Science Publishers B.V, Amsterdam, pp. 240-254, 1986 (19 pages).

Epa, "Drinking Water Criteria Document for Copper (Final Draft)", United States Environmental Protection Agency, EPA-600/X-84-190-1, pages V-1-V-28, Mar. 1985 (38 pages).

Horie, et al., "Inactivation and morphological changes of avian influenza virus by copper ions", Arch Virol, 153:1467-1472, published online Jul. 1, 2008 (6 pages).

Prausnitz, et al., "Transdermal drug delivery", Author Manuscript published in final edited form as Nat. Biotechnol., 26(11):1261-1268, Nov. 2008 (18 pages).

Stokinger, H.E. et al., "Chapter 11: Copper", in Patty's Industrial Hygiene and Toxicology: vol. 2A—Toxicology, Clayton et al., Eds., John Wiley Sons, New York, pp. 1620-1630, 1981 (16 pages).

Szunerits, et al., "Heat: A Highly Efficient Skin Enhancer for Transdermal Drug Delivery", Frontiers in Bioengineering and Biotechnology, vol. 6, Article 15, Feb. 15, 2018 (13 pages).

Tuck, et al., "3.07—Corrosion of Copper and its Alloys", Shreir's Corrosion, vol. 3, pp. 1937-1973, 2010 (38 pages).

Wright, Un-Spiked Results, Test ID: 05992-001-001, Version Type: Version, Sep. 12, 2017 (1 page).

"About the Study: Elvis COVID-19 Study Full Information", The University of Edinburgh, URL <https://www.ed.ac.uk/usher/elvis-covid-19/about-the-study>, published Jun. 24, 2020 (4 pages).

"CopperFixx Pain Relief Cream—Products", URL:https://web.archive.org/web/20160905175719/http://copperfixx.com/index/php/copperfixx/products/copperfixx-pain-relief-cream.html, Sep. 5, 2016, accessed May 2, 2023 (2 pages).

"Coronavirus: Researchers to trial salt water as Covid-19 treatment", URL <https://www.bbc.com/news/uk-scotland-edinburgh-east-fife-53170734>, Jun. 25, 2020 (2 pages).

Dutton, "Salt Water vs. COVID-19: Researchers Launch Study to Lessen Symptoms and Duration of Illness", URL <https://www.biospace.com/article/salt-water-vs-covid-19-scottish-researchers-launch-study-to-lessen-symptoms-and-duration-of-illness/>, BioSpace, Jun. 29, 2020 (6 pages).

European Extended Search Report issued in European Application No. 20760320.0, dated Oct. 25, 2022 (9 pages).

European Extended Search Report issued in European Patent Application No. EP20161252.0, dated Jun. 17, 2020 (9 pages).

Radulesco, et al., "Copper enhanced nasal saline irrigations: a safe potential treatment and protective factor for COVID-19 infection?", Rhinology Online, 3:87-88, 2020 (2 pages).

"Chapter 11.7: Crystalline Solids; Crystal Lattices and Unit Cells", in General Chemistry, Ninth Edition, Eds., Ebbing, et al., Houghton Mifflin Company, Boston, pp. 448-450, 2007 (19 pages).

"Can copper supplements fight COVID-19?", Based on Science, https://www.nationalacademies.org/based-on-science/covid-19-copper, National Academies Sciences Engineering Medicine, updated Jul. 5, 2023 (3 pages).

Raha, et al., "Is copper beneficial for COVID-19 patients?", Medical Hypotheses, https://doi.org/10.1016/j.mehy.2020.109814, 2020 (3 pages).

European Search Report issued in European Application No. EP21807576.0 dated Jan. 31, 2024 (10 pages).

"Study: To determine the anti-viral efficacy of 3VM-1000 suspension in K18-hACE2 transgenic mice model of SARS-CoV-2 infection", Texas Biomedical Research Institute, Study Sponsor 3V Medical Research Group, Inc., May 4, 2021 (10 pages).

Abbott, et al., "Statement of Work (SOW): In Vitro Assessment of the Effect of 3VM1000 Suspension on SARS-CoV-2 Infectivity", Texas Biomedical Research Institute, Jul. 22, 2020 (3 pages).

Abdel-Mottaleb, et al., "In search for effective and safe drugs against SARS-CoV-2: Part II] The role of selected salts and organometallics of copper, zinc, selenium, and iodine food supplements", ChemRxiv, doi:10.26434/chemrxiv.12234743.v1, available May 5, 2020 (13 pages).

*Drug Development & Delivery*, eBook, Respiratory Drug Development Edition, Summer 2021 (14 pages).

Dwivedi, et al., "Final Report: In vitro assessment of the effect of 3VM-1000 suspension on SARS-CoV-2 Infectivity", Texas Biomedical Research Institute, Study Sponsor 3V Medical Research Group, Inc., May 13, 2021 (14 pages).

Gordon, "Divalent Copper Compounds as Inhibitory Agents of Influenza A", Thesis submitted to the faculty of Brigham Young University, Department of Physiology and Development Biology, https://scholarsarchive.byu.edu/etd/6248, Jun. 2014 (24 pages).

Kulkarni, "Study: To determine the anti-SARS-CoV-2 effect of 3VM-1000 suspension in K18 hACE-2 mice (SOW-20-375)", Texas Biomedical Research Institute, Study Sponsor 3V Medical Research Group, Inc., dated Dec. 15, 2022 (54 pages).

Trace Minerals Ionic Copper Liquid 3mg, https://bigvits.co.uk/trace-minerals-ionic-copper-liquid-3mg-2-fl-oz-59ml.html?utm_source=google_shopping&gad_source=1&gclid=EAlaIQobChMIy_7_1fyXhQMVol1QBh2hCwiJEAQYFSABEgKn5fD_BwE, Jul. 19, 2022 (6 pages).

Correspondence from Dominic Abbott, 3V Medical Research Group, to Varun Dwivedi, Subject: Respiratory Drug & Development, includes attachment of Drug Development and Delivery ebook, email dated Jun. 27, 2022 (1 page).

\* cited by examiner

METHODS OF TREATMENT USING TOPICAL COPPER ION FORMULATIONS

CROSS-REFERENCE TO RELATED APPLICATIONS

This application is a continuation-in-part of and claims priority to U.S. patent application Ser. No. 15/865,995, filed Jan. 9, 2018, which is a continuation of U.S. patent application Ser. No. 15/265,570, filed Sep. 14, 2016, which is a continuation-in-part of U.S. patent application Ser. No. 13/841,882, filed Mar. 15, 2013, U.S. patent application Ser. No. 13/841,992, filed Mar. 15, 2013, U.S. patent application Ser. No. 13/842,310, filed Mar. 15, 2013, and U.S. patent application Ser. No. 13/842,387, filed Mar. 15, 2013 and later issued as U.S. Pat. No. 10,398,733 on Sep. 3, 2019. The entire contents of each of these patents and patent applications are hereby incorporated by reference in their entirety.

FIELD OF THE DISCLOSURE

The present disclosure pertains generally to topical treatments containing copper ions and to methods of treating conditions in various anatomical areas of the body using such formulations. Some embodiments of the present disclosure pertain to topical treatments containing copper ions and to methods of making such topical treatments wherein copper ions from copper metal are leached into a solution. In certain embodiments, the present disclosure pertains to methods of using such topical formulations to treat radiation dermatitis, damage caused by radiation therapy, or other radiation damage.

BACKGROUND OF THE DISCLOSURE

Radiation therapy is a common treatment provided to cancer patients. A large proportion of cancer patients receive adjuvant radiation therapy either with or without resection operations. Radiation therapy treatments may last several weeks, some between 4 to 6 weeks or more. Radiation dermatitis is a highly anticipated side effect of radiation therapy, with some estimating that 90% of breast cancer patients that receive radiotherapy will develop an acute radiation skin reaction. Symptoms associated with radiation dermatitis include erythema, itching, irritation, pain, moist desquamation, and reduced quality of life. The severity of such side effects is greatly influenced by treatment factors as well as factors specific to the individual. Treatment related factors include the quantitative amount of radiation dosage delivered with each treatment, the total radiation dosage delivered, the volume of the tissue treated with the radiation dosage, the type or radiation therapy used, and any additional therapies that are co-administered (e.g. chemotherapies). Factors specific to patients include age, health and smoking habits, infections, especially those associated with surgical co-treatments, and other bodily conditions both associated and not associated with the disease being treated.

Despite this common side effect and the damage and discomfort it imparts on patients, there is currently no cure. Current suggested treatments include momestason furoate cream, topical corticosteroids, emollient creams, betamethasone cream, moisturizers, skin washing with water alone or with mild soap, glycerine creams, calendula cream, deodorants. However, there is no consensus in the medical community as to which of these treatments are appropriate or substantially effective. Additionally, a number of treatments have been identified as ineffective, associated with adverse effects, and/or actually worsen radiation dermatitis symptoms. These deficient treatments include petrolatum, hydrogels, aloe extracts or creams, aqueous creams, sucralfate creams, hyaluronic acid, and oral agents. Thus, there has been an unmet medical need for effective, non-invasive treatments of radiation dermatitis without significant adverse effects.

The body, especially the skin, is further susceptible to various bodily conditions resulting from aging, environmental factors, and various external and internal causes, such conditions including sun/wind damage (including sun burns, a form of radiation damage), dry skin, age spots, pigmentation, scarring, blisters, boils, cysts, pimples, cuts, scratches, burns, abrasions, splinters, insect bites and stings, animal bites and scratches, ulcers, loss of elasticity or collagen that manifests as wrinkles and sagging skin, acne, and many types of rashes, such as measles, chicken pox, eczema, psoriasis, impetigo, shingles, postherpetic neuralgia (PHN), and rosacea, due to various underlying external and internal causes. Various topical and oral prescription and non-prescription medications and products are available to treat the foregoing skin conditions. The skin is also a carrier for bacteria, viruses and fungi, seeing as how the skin regularly comes in contact with a plethora of pathogens and microbes. Consequently, many products such as sanitizing hand and body lotions and wipes are available commercially for the purpose of reducing germs on the skin.

The prescription drugs and even many of the non-prescription drugs or products used to treat the numerous bodily conditions described above have many drawbacks including undesirable or potentially harmful side effects, high risk of harm in the event of overdose or improper use, high cost, limited effectiveness, the need for close medical monitoring, and inconvenience.

It has previously been established that copper possesses properties by which it is capable of killing, neutralizing and preventing the growth of human pathogens. It is known that many bacteria identified as human pathogens cannot survive on surfaces of copper metal. U.S. Pat. No. 8,135,466 B2 to Fuller et al. discloses a joint prosthesis having an implant body with an external surface containing an antimicrobial metal where the antimicrobial metal may be copper. U.S. Patent Application Publications No. US 2012/0071807 A1 and No. US 2012/0089068 A1 to McClure, Jr. disclose wound dressings containing a metal-based antimicrobial agent where the metal-based antimicrobial agent may be a mixture of silver ions and copper ions. Devices having an external surface of copper metal for insertion in the vagina to treat abnormal biological conditions have been proposed by Applicants in U.S. patent application Ser. No. 12/157,823 filed Jun. 13, 2008 (abandoned), Ser. No. 13/317,230 filed Oct. 12, 2011, and Ser. No. 13/464,005 filed May 4, 2012, the entire disclosures of which are incorporated herein by reference.

Topical substances containing particles of copper or its alloys have been proposed for health support uses. A product called "MesoCopper®" sold by Purist Colloids, Inc. is a colloidal copper solution containing nanoparticles of copper for use on the skin to minimize the appearance of fine lines and wrinkles. Another version of the product is sold as an ingestible mineral supplement. Copper peptides for use on the skin are also commercially available and these require peptides, i.e. small fragments of protein that have an affinity for copper to which they bind very tightly. U.S. Pat. No. 7,776,915 B2 to Morariu discloses a topical composition containing, at a minimum, a lipoic acid, a carnitine and a carnosine, where the carnosine may be chelated to zinc or copper ions. The intended use for the topical composition is to improve the appearance of aged skin. U.S. Patent Application Publication No. US2008/0195033 A1 to Eagleson et al. discloses use of a metal substance to treat diseases in the body. The metal substance is primarily a colloidal suspension and delivery of the substance to the body may require the use of electricity. Prior to the present disclosure, it has not been recognized to provide a simple solution containing copper ions for use as a topical treatment to be applied directly to anatomical tissue to treat body conditions and/or for use in conjunction with various carriers including creams, gels, lotions, foams, pastes, other solutions, suppositories, tampons, body wipes, wound dressings, skin patches and suture material to form topical treatments in which the carriers facilitate delivery of the copper ions to contact anatomical tissue depending on the anatomical area or areas of use on the body.

SUMMARY OF THE DISCLOSURE

The present disclosure pertains generally to treatments containing copper ions and to methods of treating conditions in various anatomical areas of the body using such formulations. Some embodiments of the present disclosure pertain to topical treatments containing copper ions and to methods of making such topical treatments wherein copper ions from copper metal are leached into a solution. In certain embodiments, the present disclosure pertains to methods of using such topical formulations to treat radiation dermatitis or radiation damage or irritation.

In one embodiment, the technology includes a composition for treating or preventing radiation damage in a subject in need thereof, the composition comprising a copper ion suspension; a saline solution; and one or more buffers.

In one aspect of this embodiment, the radiation damage is caused by radiation therapy. In another aspect of this embodiment, the radiation damage is radiation dermatitis.

In one aspect of this embodiment, copper ions constitute about 46 milligrams per 7.44 fluid ounces of the composition (about 0.209 milligrams per milliliter), about 35 milligrams per 7.44 fluid ounces of the composition (about 0.159 milligrams per milliliter), about 22 milligrams per 7.44 fluid ounces of the composition (about 0.100 milligrams per milliliter), or about 8.8 milligrams per 7.44 fluid ounces of the composition (about 0.0400 milligrams per milliliter).

In one embodiment, the technology includes a formulation for treating or preventing radiation damage in a subject in need thereof, the formulation comprising a copper ion suspension; a saline solution; and one or more buffers, and further comprises a cream, lotion, gel or foam base.

In one aspect of this embodiment, the copper ions constitute about 0.0002% and about 0.00627% by weight of the formulation.

In one aspect of this embodiment, the formulation is a cream. In one aspect of this embodiment, the formulation is 3VM1001.

In one embodiment, the technology includes a method of treating or preventing radiation damage in a subject in need thereof, the method comprising administering the composition comprising a copper ion suspension; a saline solution; and one or more buffers to a subject in need thereof in a therapeutically effective amount.

In one aspect of this embodiment, the radiation damage is caused by radiation therapy. In one aspect of this embodiment, the radiation damage is radiation dermatitis.

In one aspect of this embodiment, copper ions constitute about 46 milligrams per 7.44 fluid ounces of the composition (about 0.209 milligrams per milliliter), about 35 milligrams per 7.44 fluid ounces of the composition (about 0.159 milligrams per milliliter), about 22 milligrams per 7.44 fluid ounces of the composition (about 0.100 milligrams per milliliter), or about 8.8 milligrams per 7.44 fluid ounces of the composition (about 0.0400 milligrams per milliliter).

In one aspect of this embodiment, the method further comprises obtaining a first condition score from the subject before administering one or more administrations of the composition to the subject; and obtaining a second condition score from the subject after administering one or more administrations of the composition to the subject, wherein the second condition score is less than the first condition score. In a further aspect, the condition scores are VAS scores. In another further aspect, the condition scores are WOMAC scores. In another further aspect, the condition scores are RTOG scores. In another further aspect, the condition scores are Catterall scale scores. In another further aspect, the condition scores are Likert scale scores.

In some embodiments, the technology includes a method of treating or preventing radiation damage in a subject in need thereof, the method comprising administering a solution comprising a copper ion suspension; a saline solution; and one or more buffers. In one embodiment, the technology includes a method of treating or preventing radiation damage in a subject in need thereof, the method comprising administering a formulation comprising a copper ion suspension; a saline solution; and one or more buffers, and further comprising a cream, lotion, gel or foam base to a subject in need thereof in a therapeutically effective amount.

In one aspect of this embodiment, the radiation damage is caused by radiation therapy. In one aspect of this embodiment, the radiation damage is radiation dermatitis.

In one aspect of this embodiment, copper ions constitute about 0.0002% and about 0.00627% by weight of the formulation.

In one aspect of this embodiment, the formulation is a cream. In one aspect of this embodiment, the formulation is 3VM1001.

In some embodiments, the present disclosure provides methods of treating radiation dermatitis resulting by administering a pharmaceutically acceptable topical formulation comprising copper ions 1-3 times daily to a human in need of such treatment. In certain embodiments, the radiation dermatitis treated is a result of anti-cancer radiation therapy.

In some aspects of the present disclosure, a patient with radiation toxicity achieves a Visual Analog Scale (VAS) score that is at least 15 units lower than the baseline VAS score following treatment with a copper ion containing formulation of the present disclosure. In some aspects of the present disclosure, a VAS score that is at least 25 units lower than the baseline VAS score is achieved.

In some aspects of the present disclosure, a patient with radiation toxicity achieves a Western Ontario and McMaster Universities Arthritis Index (WOMAC) score that is at least 4 units lower than the baseline WOMAC score, following treatment with a copper ion containing formulation of the present disclosure.

In some aspects of the present disclosure, a patient with radiation toxicity achieves a reduction in a score using Radiation Therapy Oncology Group acute radiation morbidity scoring criteria (RTOG), following treatment with a copper ion containing formulation of the present disclosure. In other aspects of the present disclosure, a patient with radiation toxicity achieves a reduction in a score using the Catterall scale, following treatment with a copper ion containing formulation of the present disclosure. In other aspects of the present disclosure, a patient with radiation toxicity achieves a reduction in a score using the Likert scale, following treatment with a copper ion containing formulation of the present disclosure.

Some embodiments provide a pharmaceutically acceptable copper ion formulation that is a cream, lotion, gel or a foam, and methods of treatment wherein said cream, lotion, gel or foam is applied topically. In certain embodiments, the pharmaceutically acceptable formulation is a cream, such as 3VM1001 cream. The present disclosure includes formulations wherein at least 10 µg/mL copper ion is present in the liquid phase. In some embodiments, the pharmaceutically acceptable formulation comprises about 11.5 µg/mL copper ion in the liquid phase. In some embodiments, the pharmaceutically acceptable formulation comprises about 15 µg/mL.

In some embodiments, a copper ion formulation according to the present disclosure is applied topically every day. In other embodiments, a copper ion formulation according to the present disclosure is applied topically 1, 2, 3, 4 or 5 times per day. In certain embodiments, a copper ion formulation according to the present disclosure is applied every 2-24 hrs. In certain embodiments, a copper ion formulation according to the present disclosure is applied as needed.

In certain embodiments, 0.5-10 g of a copper ion formulation is applied at each administration. In some of these embodiments, 0.5 g, 1 g, 1.5 g, 2 g, 2.5, 3, 3.5, 4, 4.5 or 5 g is applied at each administration. In certain embodiments, 0.5 g, 1 g, 1.5 g, 2 g, 2.5, 3, 3.5, 4, 4.5 or 5 g of a copper ion containing cream is applied at each administration. In certain embodiments, 2 g of a copper ion containing cream is applied 1-3 times/day. In some embodiments, 2 g of a copper ion containing cream is applied 3 times/day.

The present disclosure further provides methods of making a copper ion cream from wherein the copper present in the liquid phase is substantially enhanced. In some of these embodiments, the copper concentration in the liquid phase is substantially enhanced compared to the copper concentration in the liquid phase of a bulk suspension used to prepare the cream. In certain embodiments, the copper concentration in the liquid phase of the cream is at least 5-10 µg/mL or at least 10-15 µg/mL. In certain embodiments, the copper concentration in the liquid phase of the cream is about 11.5 µg/mL. In some embodiments, the copper concentration in the liquid phase of the cream is about 15 µg/mL.

Some embodiments provide a pharmaceutically acceptable copper ion formulation wherein copper ions are the only active ingredients. In certain embodiments, the pharmaceutically acceptable formulation is a cream consisting of a cream base, such as VersaBase® or Vanicream®, and a copper ion suspension or solution. In certain embodiments, the copper ion suspension or solution consists of a saline solution, one or more buffers (e.g. acetic acid, acetate, and/or phosphate) disposed in the saline solution, and copper ions disposed in solution.

According to an aspect of the present disclosure, a topical copper ion treatment is prepared by a process whereby copper ions from copper metal leach into a biocompatible solution. The copper metal in solid form is placed into the solution in a sealed vessel, and the sealed vessel is placed in an oven to heat or maintain the solution at a temperature equal or substantially equal to 37° Celsius for a predetermined period of time during which copper ions leach from the copper metal into the solution, where they may form insoluble salts by combining with negatively charged counter-ions, such as phosphate. Alternatively, the temperature may be equal to or substantially equal to 50° Celsius or equal to or substantially equal to 70° Celsius. After the period of time has expired, the solution is separated from the copper metal and constitutes a copper ion-containing solution that can be used as a copper ion treatment for topical application to anatomical tissue in various areas of the body to treat various body conditions. Preferably, the biocompatible solution is a saline solution and the copper metal is pure copper. A copper ion-containing solution or suspension obtained in accordance with a preferred process results in an amount of copper ions equal or substantially equal to 46 mg present in 7.44 ounces of the copper ion-containing solution or suspension.

According to another embodiment of the present disclosure, a bulk suspension comprising precipitated copper salts is prepared by incubating a buffered saline solution with copper metal. The resulting bulk suspension is subsequently combined with a cream base to yield a cream wherein a substantial proportion of the copper from the bulk suspension is found in the soluble phase. In certain embodiments, at least 5 µg/mL, 7 µg/mL, 9 µg/mL, 11 µg/mL, or at least 15 µg/mL of copper is found in the soluble phase. In some embodiments, the liquid phase of the cream contains about 11.5 µg/mL. In some embodiments, the liquid phase of the cream contains about 15 µg/mL.

The copper ion-containing solution can be combined with various carriers to facilitate application or delivery of the copper ion-containing solution to anatomical tissue in accordance with the anatomical area or areas of use. Suitable carriers include creams, lotions, gels, foams, pastes, other solutions, tampons, suppositories, body wipes, wound dressings, skin patches and suture material to obtain other forms of copper ion treatments. Various devices such as containers, bottles and tubes can be used to dispense the copper ion treatments in a manner best suited for the form of copper ion treatment and/or the intended anatomical area or areas of use. The copper ion treatments are particularly advantageous for use on anatomical tissue of the dermatological areas of the body.

DETAILED DESCRIPTION OF EMBODIMENTS

Figure 3:
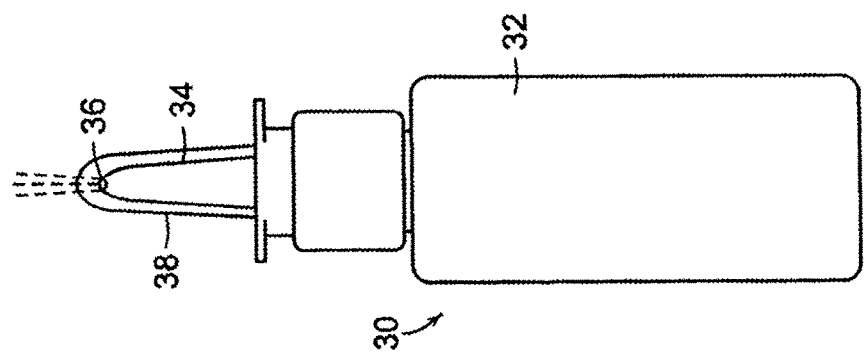
FIG. 3 is a side view of a bottle containing a copper ion treatment wherein the bottle is squeezable to dispense the copper ion treatment from a dropper on the bottle.

Provided herein are topical formulations comprising copper ions for the treatment of a variety of conditions, including inflammatory conditions. In particular, methods of treating radiation dermatitis or radiation damage using topical copper ion formulations such as a copper ion cream are provided. Inasmuch as the present disclosure is subject to many variations, modifications and changes in detail, it is intended that all subject matter discussed above or shown in the accompanying drawings be interpreted as illustrative only and not be taken in a limiting sense.

In some embodiments, a solution containing copper ions, i.e. copper ion-containing solution, for use as a topical treatment containing copper ions, i.e. topical copper ion treatment, to treat body conditions is produced according to a process or method by which copper ions from copper metal are leached into an appropriate biocompatible solution. As used herein, "copper metal" means pure copper (99.5% or greater copper after processing) and copper alloys such as brasses, bronzes, copper-nickels and copper-nickel-zincs. Preferably, pure copper is used as the copper metal. Example 1 describes the steps involved in producing an amount of copper ion-containing solution equal or substantially equal to 7.44 ounces.

In other embodiments, a suspension containing a copper salt precipitate is combined with a cream base to create a copper ion cream, wherein a substantial proportion of the copper ions are found in the liquid phase of the cream. In certain embodiments, at least 5 μg/mL, 7 μg/mL, 9 μg/mL or 11 μg/mL of copper is found in the soluble phase. In some embodiments, the liquid phase of the cream contains about 11.5 μg/mL of copper. Example 34 describes the steps involved in preparing a cream with about 11.5 μg/mL of copper in the soluble phase.

In some embodiments, the solution containing copper ions is produced using substantially pure copper. In embodiments, the solution containing copper ions is produced by adding an appropriate amount of solution in a vessel with copper. In some embodiments, additional solution is placed in the vessel to decrease the concentration of the copper ions leached into the solution. In some embodiments, less solution is placed in the vessel to increase the concentration of the copper ions leached into the solution.

In some embodiments, the solution is buffered. In some embodiments, the buffer comprises at least one of acetate, acetic acid, phosphate, a phosphoric acid, or at least one salt of acetate, acetic acid, phosphate, or phosphoric acid. In some embodiments, the solution requires no buffer, or the solution is substantially free of buffers or buffering agents. In some embodiments, the solution is a saline solution.

In some embodiments, the copper load is disposed into the solution for a predetermined time between about 0.5 hours and several days (e.g., 1, 2, 3, 4, 5, 6, 7, or 10 days), several weeks (e.g., 1, 2, 3, 4, 5, or 6 weeks), or several months (e.g., 1, 2, 3, 4, 5, 6, or 12 months). In some embodiments the predetermined time is between about 0.5 hours and about 72 hours. In some embodiments, the time is about 0.5, about 1, about 1.5, about 2, about 2.5, about 3, about 4, about 5, about 6, about 12, about 18, about 24, about 36, about 48, about 60, or about 72 hours.

In some embodiments, the solution with the copper load disposed in it is heated or cooled to a predetermined temperature. In some embodiments, the temperature is brought to between about 20° C. (i.e. about room temperature) to about 100° C. In some embodiments, the temperature is brought to between about 20° C. and 70° C. In some embodiments, the temperature is brought to between about 35° C. and 70° C. In some embodiments, the temperature is brought to between about 35° C. and 50° C. In some embodiments, the temperature is brought to about 37° C. and maintained for a predetermined period of time. In some embodiments, the temperature is brought to about 50° C. and maintained for a predetermined period of time. In some embodiments, the temperature is brought to between about 20° C. and 35° C. In some embodiments, the temperature is brought to between about 50° C. and 70° C. In some embodiments, the temperature is brought to between about 70° C. and 100° C.

Inasmuch as the present disclosure is subject to many variations, modifications and changes in detail, it is intended that all subject matter discussed above or shown in the accompanying drawings be interpreted as illustrative only and not be taken in a limiting sense.

EXAMPLES

Example 1

7.44 ounces of biocompatible saline solution buffered with acetic acid and sodium acetate to a pH of 5 (±0.4) is placed in a container or vessel with a tight, removable lid to minimize evaporation. The container is placed in an incubator or oven at a temperature of 37° Celsius (±1° C.). When the saline solution has reached 37° Celsius, 102 grams of pure copper metal in solid form is placed in the heated solution within the container, and the container with the tight lid thereon is placed in the incubator at 37° Celsius for 24 hours. During the 24 hour period, copper ions from the copper metal leach into the solution. At the end of the 24 hour period, the container is removed from the incubator and the copper metal is removed or separated from the solution. The amount of solution remaining after removal or separation of the copper metal therefrom constitutes the copper ion-containing solution and should be essentially 7.44 ounces with minimal evaporation. The copper ion-containing solution produced according to this process contains copper ions in an amount equal or substantially equal to 46 milligrams when analyzed for copper content by inductively coupled plasma/optical emission spectroscopy (ICP/OES). The copper ion-containing solution is stored at room temperature and is ready for use in this form as a topical copper ion treatment to be applied to anatomical tissue to treat body conditions. In addition, the copper ion-containing solution is ready for use in conjunction with various carriers including creams, gels, lotions, foams, pastes, other solutions, suppositories, tampons, body wipes, wound dressings, skin patches and suture materials to form topical copper ion treatments in which the carriers facilitate delivery of the copper ion treatments to contact anatomical tissue to treat body conditions.

The solid pure copper metal in Example 1 may be in the form of one or more sheets of pure copper metal, typically in the range of 0.03 to 0.06 inch thick, of appropriate length and width to provide the 102 grams of pure copper metal. In practice, the process described in Example 1 has been carried out using as the copper metal four vaginal therapeutic devices made of pure copper in accordance with Applicants' prior patent application Ser. No. 13/464,005 previously incorporated herein by reference in its entirety. In this case, each vaginal therapeutic device used was 3.25 Inches long by 0.750 inch wide with a wall thickness of 0.031 inch providing 25.5 grams of pure copper. The biocompatible saline solution used in the process described in Example 1 is commercially available from B. Braun Medical. As an alternative to the biocompatible saline, vaginal simulating fluid (VSF) buffered with acetic acid to a pH of 5 (±0.4) can be used as the biocompatible solution, but will produce less leaching of copper ions from copper metal over the 24 hour period. The VSF can be prepared in accordance with published literature, e.g. Owen, D. H., Katz, D. F., "A Vaginal Fluid Simulant", Contraception, pages 91-95 (1999). The process described in Example 1 can be modified to eliminate the step of heating the solution prior to placement of the copper metal therein. In the latter case, the copper metal and unheated solution are placed in the container, the container with the tight lid thereon is placed in the Incubator at 37° Celsius and, once the solution has reached 37° Celsius, the container with the heated solution and copper metal therein is allowed to remain in the oven for 24 hours. The copper metal can be removed or separated from the solution in various ways, such as by lifting the metal out of the solution or pouring the solution alone into another container. Of course, the quantities of biocompatible saline and solid copper mental used in Example 1 can be proportionately increased to produce a greater amount of copper ion-containing solution with each process.

The copper ion-containing solution is believed to have the greatest effectiveness for treating a wide range of body conditions when the solution contains the amount of copper ions leached into the saline from the 46 mg copper metal over a 24 hour period as described in Example 1. However, it should be appreciated that the process described in Example 1 can be modified to obtain lower copper ion concentrations by adjusting the length of time that the container containing the heated saline and copper metal is allowed to remain in the incubator or oven as explained below in Examples 2, 3 and 4.

Example 2

This Example follows the steps of Example 1 except that the container containing the saline and copper metal to remain in the oven at 37° C. for one hour to obtain a copper ion-containing solution that contains an amount of copper ions equal or substantially equal to 8.8 mg.

Example 3

This Example follows the steps of Example 1 except that the container containing the saline and copper metal to remain in the oven at 37° C. for eight hours to obtain a copper ion-containing solution that contains an amount of copper ions equal or substantially equal to 22 mg.

Example 4

This Example follows the steps of Example 1 except that the container containing the saline and copper metal to remain in the oven at 37° C. for 72 hours to obtain a copper ion-containing solution that contains an amount of copper ions equal or substantially equal to 35 mg.

The copper ion-containing solution in its original form. i.e. at the end of the processes of Examples 1-4, can be applied directly to anatomical tissue in various anatomical areas of the body as a copper ion treatment to treat various body conditions. Many types of containers or bottles can be used to hold a quantity of the copper ion-containing solution and to dispense or apply the copper ion-containing solution to anatomical tissue in accordance with the intended anatomical area or areas of use. The copper ion-containing solution may also be used in conjunction with various carriers including creams, lotions, gels, foams, pastes, other solutions, tampons, suppositories, body wipes, wound dressings such as band aids and pads, skin patches and suture material to form copper ion treatments that facilitate delivery or application of the copper ion-containing solution, and therefore the copper ions, to anatomical tissue. Creams, lotions, gels, foams and pastes may be used when it is advantageous to alter the consistency of the copper ion-containing solution from its original form to obtain a thicker copper ion treatment to facilitate its delivery or application to anatomical tissue. As a result of the copper ions contacting anatomical tissue when the copper ion treatments are applied thereto, local and systemic therapeutic effects are realized including reducing and/or preventing the symptoms of radiation damage (e.g. radiation dermatitis), antibacterial, antimicrobial, antiseptic, antifungal, antiviral, anti-pathogenic, anti-inflammatory, spermicidal, neutralization of free radicals, promotion of healing and tissue repair, prevention of biofilm, and immune-boosting effects. In particular, these effects are realized when the copper ion treatments are used on anatomical tissue in the genital-rectal areas, the oral-respiratory-otic areas and the dermatological areas of the body since the anatomical tissue in these areas is favorable for local and systemic delivery of drugs and medicaments.

In accordance with an aspect of the present disclosure, the copper ion-containing solution is combined with an appropriate topical cream base to form a copper ion-containing cream, i.e. copper ion cream in which the amount of copper ion-containing solution is preferably in the range of 5% to 30% by weight of the total weight of the copper ion cream. Examples 5, 6, 7 and 8 pertain to copper ion creams made in accordance with this aspect of the present disclosure using the copper ion-containing solution of Example 1.

Example 5

An appropriate amount of copper ion-containing solution is combined with a biocompatible topical cream base to form a copper ion cream in which the copper ion-containing solution constitutes 5 percent of the total weight of the copper ion cream.

Example 6

An appropriate amount of copper ion-containing solution is combined with a biocompatible topical cream base to form a copper ion cream in which the copper ion-containing solution constitutes 10 percent of the total weight of the copper ion cream.

Example 7

An appropriate amount of copper ion-containing solution is combined with a biocompatible topical cream base to form a copper ion cream in which the copper ion-containing solution constitutes 20 percent of the total weight of the copper ion cream.

Example 8

An appropriate amount of copper ion-containing solution is combined with a biocompatible topical cream base to form a copper ion cream in which the copper ion-containing solution constitutes 30 percent of the total weight of the copper ion cream.

Various topical cream bases can be used as the carrier for the copper ion-containing solution in order to form the copper ion creams of Examples 5, 6, 7 and 8. One suitable topical cream base that can be used is VersaBase® cream made by Professional Compounding Centers of America (PCCA) of Houston, Tex. Another suitable topical cream base that can be used in the copper ion creams is Vanicream® made by Pharmaceutical Specialties, Inc. of Rochester, Minn. The copper ion creams are effective against the body conditions being treated when the only active ingredient in the copper ion creams directed at the underlying condition is the copper ion-containing solution. However, the copper ion creams could contain other ingredients added to the topical cream base that are not active ingredients with respect to the underlying condition being treated such as preservatives, penetrating additives, bioadhesives and stability aids. Preferably, a total weight of at least 70 grams, more preferably 80 grams, of the copper ion creams in the various strengths. i.e. 5 percent, 10 percent, 20 percent and 30 percent of copper ion-containing solution relative to the total weight of the copper ion cream, will be provided for use in containers, bottles, or tubes from which the copper ion creams can be dispensed. It should be appreciated that copper ion creams can be made using the alternative copper ion-containing solutions described above.

According to a further aspect of the present disclosure, a topical copper ion treatment in the form of a copper ion-containing gel, i.e. copper ion gel, is composed of the copper ion-containing solution and a suitable topical gel base as illustrated below by Examples 9, 10, 11 and 12, which utilize the copper ion-containing solution of Example 1. The amount of the copper ion-containing solution in the copper ion gel is preferably in the range of 5% to 30% by weight of the total weight of the copper ion gel.

Example 9

An appropriate amount of copper ion-containing solution is combined with a biocompatible topical gel base to form a copper ion gel in which the copper ion-containing solution constitutes 5 percent of the total weight of the copper ion gel.

Example 10

An appropriate amount of copper ion-containing solution is combined with a biocompatible topical gel base to form a copper ion gel in which the copper ion-containing solution constitutes 10 percent of the total weight of the copper ion gel.

Example 11

An appropriate amount of copper ion-containing solution is combined with a biocompatible topical gel base to form a copper ion gel in which the copper ion-containing solution constitutes 20 percent of the total weight of the copper ion gel.

Example 12

An appropriate amount of copper ion-containing solution is combined with a biocompatible topical gel base to form a copper ion gel in which the copper ion-containing solution constitutes 30 percent of the total weight of the copper ion gel.

Various topical gel bases can be used as a carrier for the copper ion-containing solution in order to form the copper ion gels. An example of a suitable topical gel base that can be used in Examples 9-12 is VersaBase® gel made by PCCA. As explained above for the copper ion creams, the copper ion gels will be effective when the only active ingredient in the copper ion gels is the copper ion-containing solution, but other ingredients that are inactive with respect to the underlying condition being treated can be added to the topical cream gels. Preferably, a total weight of at least 70 grams, more preferably 80 grams, of the copper ion gels in the various strengths, i.e. 5 percent 10 percent, 20 percent and 30 percent of copper ion-containing solution relative to the total weight of the copper ion gel, is provided for use in containers, bottles or tubes from which the copper ion gels can be dispensed. Also, copper ion gels can be made using the alternative copper ion-containing solutions. Copper ion gels can be made having a thin, fluidic consistency, and such gels may be used as copper ion serums.

A topical copper ion treatment in the form of a copper ion-containing lotion, i.e. copper ion lotion, according to an additional aspect of the present disclosure is composed of the copper ion-containing solution and a suitable topical lotion base as represented by Examples 13, 14, 15 and 16. Examples 13-16 employ the copper ion-containing solution of Example 1, but copper ion lotions could be made using the alternative copper ion-containing solutions. The amount of the copper ion-containing solution in the copper ion lotion is preferably in the range of 5% to 30% by weight of the total weight of the copper ion lotion. Copper ion gels can be made having a thin, fluidic consistency, and such gels may be used as copper ion serums.

Example 13

An appropriate amount of copper ion-containing solution is combined with a biocompatible topical lotion base to form a copper ion lotion in which the copper ion-containing solution constitutes 5 percent of the total weight of the copper ion lotion.

Example 14

An appropriate amount of copper ion-containing solution is combined with a biocompatible topical lotion base to form a copper ion lotion in which the copper ion-containing solution constitutes 10 percent of the total weight of the copper ion lotion.

Example 15

An appropriate amount of copper ion-containing solution is combined with a biocompatible topical lotion base to form a copper ion lotion in which the copper ion-containing solution constitutes 20 percent of the total weight of the copper ion lotion.

Example 16

An appropriate amount of copper ion-containing solution is combined with a biocompatible topical lotion base to form a copper ion lotion in which the copper ion-containing solution constitutes 30 percent of the total weight of the copper ion lotion.

Various topical lotion bases can be used as a carrier for the copper ion-containing solution in the copper ion lotions of Examples 13-16. One suitable topical lotion base that can be used is VersaBase® lotion made by PCCA. As explained above for the copper ion creams and gels, the copper ion lotions will be effective against the body conditions being treated when the only active ingredient in the copper ion lotions is the copper ion-containing solution, but other inactive ingredients could be added to the topical lotion base. Preferably, a total weight of at least 70 grams, more preferably 80 grams, of the copper ion lotions in the various strengths, i.e. 5 percent, 10 percent, 20 percent and 30 percent of copper ion-containing solution relative to the total weight of the copper ion lotion, will be provided for use in containers, bottles or tubes from which the copper ion lotions can be dispensed.

According to another aspect of the present disclosure, a topical copper ion treatment in the form of a copper ion-containing foam, i.e. copper ion foam, is composed of the copper ion-containing solution and a suitable foam base. Examples 17, 18, 19 and 20 set forth below pertain to copper ion foams or foamable solutions made in accordance with this aspect of the present disclosure using the copper ion-containing solution of Example 1, however copper ion foams or foamable solutions can be made using the alternative copper ion-containing solutions. The amount of the copper ion-containing solution in the copper ion foam or foamable solution is preferably in the range of 5% to 30% by weight of the total weight of the copper ion foam or foamable solution.

Example 17

An appropriate amount of copper ion-containing solution is combined with a biocompatible topical foam base to form a copper ion foam or foamable solution in which the copper ion-containing solution constitutes 5 percent of the total weight of the copper ion foam or foamable solution.

Example 18

An appropriate amount of copper ion-containing solution is combined with a biocompatible topical foam base to form a copper ion foam or foamable solution in which the copper ion-containing solution constitutes 10 percent of the total weight of the copper ion foam or foamable solution.

Example 19

An appropriate amount of copper ion-containing solution is combined with a biocompatible topical foam base to form a copper ion foam or foamable solution in which the copper ion-containing solution constitutes 20 percent of the total weight of the copper ion foam or foamable solution.

Example 20

An appropriate amount of copper ion-containing solution is combined with a biocompatible topical foam base to form a copper ion foam or foamable solution in which the copper ion-containing solution constitutes 30 percent of the total weight of the copper ion foam or foamable solution.

Various topical foam bases can be used as a carrier for the copper ion-containing solution in order to form the copper ion foams or foamable solutions. Depending on the foam base used in Examples 17-20, the combination of foam base and copper ion-containing solution may be in the form of a foam. Alternatively, some foam bases that may be used will result in a foamable solution when combined with the copper ion-containing solution, and the foamable solutions will typically require an appropriate dispenser to create the actual foam. An example of a suitable topical foam base that can be used is VersaBase® foam made by PCCA. When using VersaBase® as the foam base in Examples 17-20, a foamable solution is obtained and requires a foam dispenser to create the foam. As explained above for the copper ion creams, gels and lotions, the copper ion foams win be effective against the body conditions being treated with the only active ingredient therein being the copper ion-containing solution. However, other ingredients that are inactive with respect to the condition being treated can be added to the topical foam base. It is preferred that a total weight of at least 70 grams, more preferably 80 grams, of the copper ion foams or foamable solutions in the various strengths, i.e. 5 percent, 10 percent, 20 percent and 30 percent of copper ion-containing solution relative to the total weight of the copper ion foam or foamable solution, be provided in dispensers from which the copper ion foams can be dispensed.

According to a further aspect of the present disclosure, a topical copper ion treatment in the form of a copper ion-containing paste, i.e. copper ion paste, is composed of the copper ion-containing solution and a suitable paste base. Example 21 set forth below pertains to a copper ion toothpaste made in accordance with this aspect of the present disclosure using the copper ion-containing solution of Example 1, but copper ion pastes can also be made using the alternative copper ion-containing solutions. The amount of the copper ion-containing solution in the copper ion pastes is preferably in the range of 5% to 30% by weight of the total weight of the copper ion paste.

Example 21

An appropriate amount of copper ion-containing solution is combined with a toothpaste base material to form a copper ion toothpaste in which the copper ion-containing solution constitutes in the range of 5 percent to 30 percent of the total weight of the copper ion toothpaste.

The toothpaste base material used in Example 21 can be a commercially available toothpaste including any of the toothpastes marketed and sold under the major brand names. A toothpaste made in accordance with Example 21 is advantageous for reducing and/or preventing the symptoms of radiation damage (e.g. radiation dermatitis) affecting the mouth, treating bad breath, sore gums, gum disease, plaque, biofilm and tooth decay when used on a daily basis in place of a person's regular toothpaste.

According to a further aspect of the present disclosure, the copper ion-containing solution can be combined with various base solutions to form alternative copper ion solutions. Example 22 set forth below pertains to a copper ion mouthwash made in accordance with this aspect of the present disclosure using the copper ion-containing solution of Example 1, but copper ion solutions can also be made using the alternative copper ion-containing solutions of Examples 2-4. The amount of copper ion-containing solution in the alternative copper ion solution is preferably in the range of 5% to 30% by weight of the total weight of the copper ion solution.

Example 22

An appropriate amount of copper ion-containing solution is combined with a mouthwash base solution to form a copper ion mouthwash in which the copper ion-containing solution constitutes in the range of 5 percent to 30 percent of the total weight of the copper ion mouthwash.

The mouthwash base solution used in Example 22 can be a commercially available mouthwash including any of the mouthwashes marketed and sold under the major brand names. A mouthwash made in accordance with Example 22 is advantageous for reducing and/or preventing the symptoms of radiation damage (e.g. radiation dermatitis) affecting the mouth, treating bad breath, sore gums, periodontal disease and tooth decay when used on a daily basis.

The examples described above pertaining to carriers in the nature of lotions, gels, foams and other solutions are particularly well suited for creating copper ion treatments in the nature of copper ion soaps by using as carriers lotion, gel, foam or other solution bases containing a soap component. The copper ion soaps could be designed for use as body soaps or as dish soaps.

Figure 1:
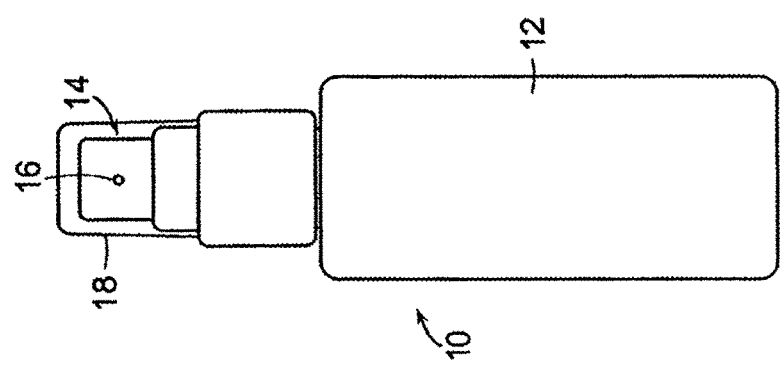
FIG. 1 is a front view of a bottle containing a copper ion treatment and having a spray pump nozzle for dispensing the copper ion treatment.

FIG. 1 depicts a device 10 useful for dispensing the copper ion treatments, particularly the copper ion-containing solutions in their original form, e.g. the form resulting from Examples 1-4, and the copper ion lotions. The device 10 comprises a container or bottle 12 for holding the copper ion-containing solution and having a spray pump nozzle 14 with an outlet orifice 16. The spray pump nozzle 14 is resiliently biased, typically by a spring, in an upward direction away from the container 12 but is depressible in a downward direction toward the container 12 to effect the spray pump action. Each time the spray pump nozzle is manually depressed the full amount, typically using a finger of the hand holding the container, a predictable amount of copper ion-containing solution is discharged in the form of a spray or stream from the outlet orifice 16. The container 12 may include a removable protective cover 18 for being disposed over the spray pump nozzle 14 between uses. In use, the outlet orifice 16 is placed in line with anatomical tissue to be treated at a close enough distance that the tissue is within the range of the spray or stream dispensed from the outlet orifice. The spray pump nozzle 14 is then depressed the full amount using a finger, causing the predictable amount of copper ion-containing solution to be delivered or sprayed onto the anatomical tissue. The spray pump nozzle 14 can, of course, be depressed multiple times to deliver multiple sprays or streams of the copper ion-containing solution to the tissue. The device 10 could also be adapted to dispense the copper ion lotions in a similar manner, although in such case the copper ion lotions would typically be dispensed in the form of a ribbon, mass or stream of material. In the latter case, the copper ion lotions could be dispensed directly on the tissue to be treated, or on the palm or fingers of a hand which is then used to apply the lotions on the tissue to be treated. The copper ion lotions may be best suited for use on the skin, on the external genital and rectal areas, and in the vagina.

Figure 2:
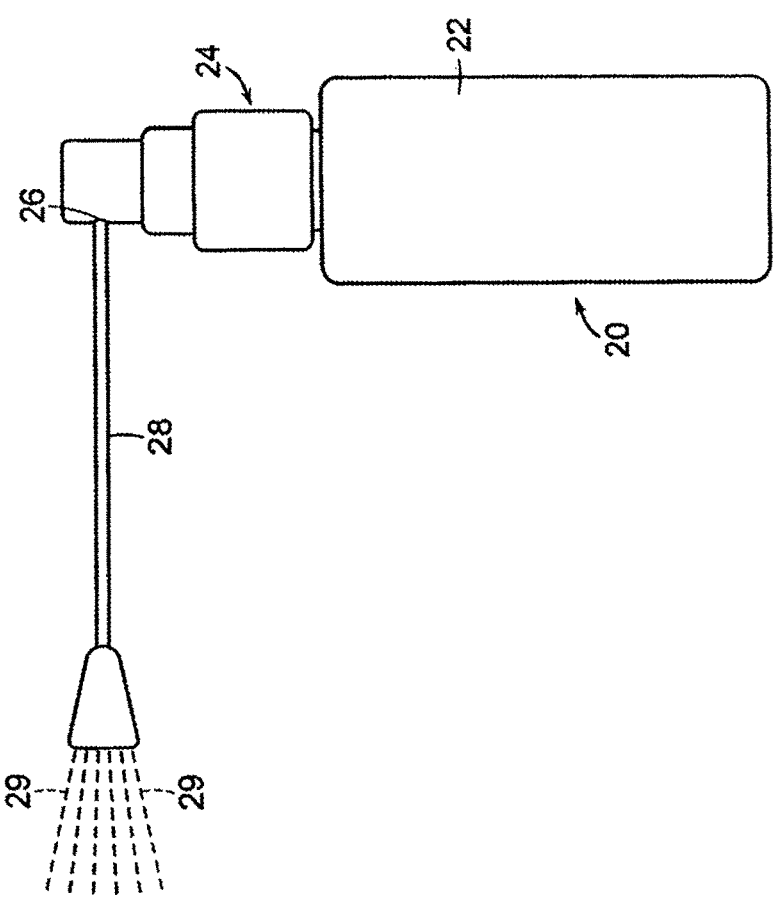
FIG. 2 is a side view of a bottle containing a copper ion treatment and having a spray pump nozzle with an elongate extension for dispensing the copper ion treatment.

Another device 20 useful for dispensing the copper ion treatments, particularly the copper ion-containing solution in its original form, is shown in FIG. 2. The device 20 is similar to the device 10 and comprises a container or bottle 22 having a spray pump nozzle 24 with an outlet orifice 26. The device 20, however, further includes an elongate hollow extension 28 attached to the spray pump nozzle 24. The extension 28 has a first end coupled with the outlet orifice 26 of the spray pump nozzle 24 and has an opposed second end with a wider end surface having a discharge opening 29. Preferably, a plurality of discharge openings 29 are provided along the wider end surface as shown in dotted lines in FIG. 2 to obtain a wider spray pattern as indicated by dotted lines. Each time the spray pump nozzle 24 is manually depressed the full amount, a predictable amount of copper ion treatment is released in spray form from the discharge openings 29 at the end of the extension 28. The wider end surface and plurality of discharge openings at the second end of the extension provides a wider spray pattern than the device 10. The device 20 could be designed without the spray pump nozzle, with the container 22 being squeezable to force the copper ion treatment to be discharged from the discharge opening(s) 29. The extension 28 may be selectively detachable/attachable to the spray pump nozzle 24 for ease of storage of the device 20. The device 20 may include a removable protective cover (not shown) for being placed over the nozzle 24 between uses. The device 20 is particularly useful as an atomizer for dispensing the copper ion treatments to contact anatomical tissue deeper within the mouth, throat and airway.

The device 30 depicted in FIG. 3 is also useful for dispensing the copper ion treatments, particularly the copper ion-containing solution in its original form. The device 30 comprises a squeezable container or bottle 32 for holding the copper ion treatment and having a tapered dropper or extension 34 with an outlet orifice 36 attached to a cap on the container 32. In use, the container 32 is positioned so that the outlet orifice 36, which is located at the tip of the dropper, faces anatomical tissue to be treated. The container 32 is then squeezed with the fingers and, in response to such finger pressure, individual drops of a predictable amount of copper ion treatment are released from the outlet orifice 36. Alternatively, the extension 34 can be designed to discharge the copper ion treatment in the form of a spray as shown in dotted lines in FIG. 3, which would be particularly useful as a nasal/ear spray. The tapered configuration of the dropper/extension 34 facilitates its placement in the nostril (nasal cavity) and ear (ear canal). The container 32 may include a removable protective cover 38 for being disposed over the dropper 34 between uses. The device 30 is particularly useful for dispensing the copper ion treatments to contact anatomical tissue within the nose (nostrils), ears (ear canal), skin and nails.

Figure 4:
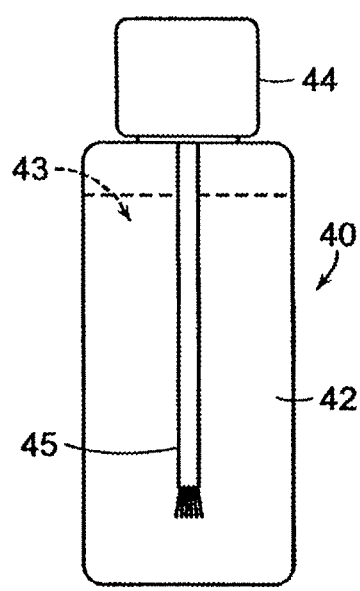
FIG. 4 is a side view of a bottle containing a copper ion treatment and having a brush for applying the copper ion treatment to anatomical tissue.

An additional device 40 for dispensing the copper ion treatments is shown in FIG. 4. The device 40 comprises a container or bottler 42 for holding the copper ion treatment and having a removable cap 44 with a brush 45 attached to an underside of the cap. Typically, the cap 44 will be screwed onto a neck of the container 42. When the cap 44 is disposed on the container 42, the brush 45 extends into the container and is disposed within the copper ion treatment 43. Upon removal of the cap 44 from the container 42, the cap 44 may be manipulated using the fingers and hand to contact anatomical tissue to be treated with the brush 45 in order to deposit the copper ion treatment from the brush 45 onto the anatomical tissue. The device 40 would be particularly useful for applying the copper ion treatments on the skin and nails. The brush 45 could be eliminated from the cap 44, in which case the device 40, if sized appropriately, would be advantageous for holding a copper ion solution such as a copper ion mouthwash.

Figure 5:
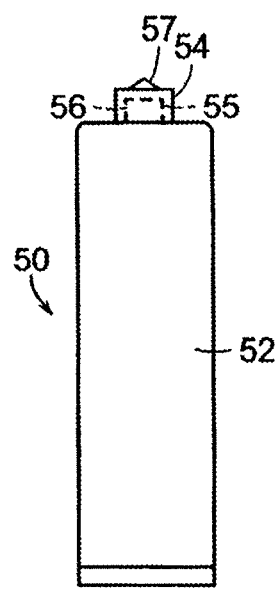
FIG. 5 is a side view of a tube containing a copper ion treatment wherein the tube is squeezable to dispense the copper ion treatment.

The device 50 illustrated in FIG. 5 is particularly useful for dispensing the copper ion treatments formed as creams, lotions, gels and pastes. The device 50 comprises a container 52 in the form of a squeezable tube for holding the copper ion treatment and having a removable cap 54 disposed on an open end or neck 56 of the tube. Typically the cap 54 will be threaded onto an external thread 55 on the neck 56 of the tube. The cap 54 may optionally have a piercing formation 57 that may be used to puncture an optional seal covering the open neck 56 prior to the first use. Upon removal of the cap 54, the piercing formation 57 is placed against the seal, and the cap 54 is pushed in the direction of the tube 52 to puncture the seal. Once the seal is penetrated, the tube 52 can be squeezed, preferably from the bottom of the tube working upward, causing the copper ion treatment to be dispensed from the open neck 56 of the tube. The device 50 is particularly well suited for dispensing the copper ion treatments onto the fingers or palm of a hand that is then used to apply the treatments to anatomical tissue, particularly the tissue of the skin and the external genital and rectal areas. However, the copper ion treatments could be squeezed directly on the anatomical tissue to be treated. In addition, when the copper ion treatment is in a paste or other suitable form for use as a toothpaste, the device 50 is particularly well suited for dispensing the copper ion treatment onto a toothbrush in a conventional manner. As explained further below, the device 50 is particularly well suited for use with a vaginal applicator.

Figure 6:
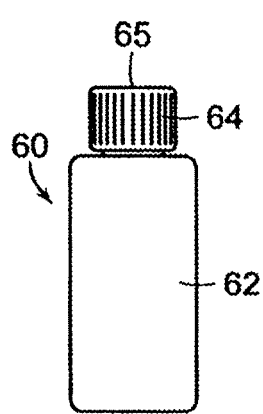
FIG. 6 is a side view of an alternative bottle that is squeezable to dispense a copper ion treatment and showing the bottle in a dosed condition.
Figure 7:
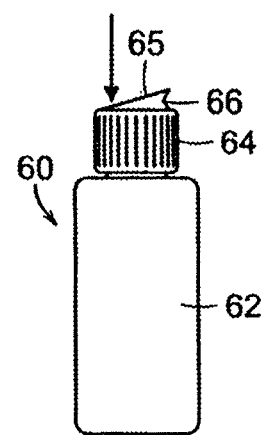
FIG. 7 is a side view of the bottle of FIG. 6 showing the bottle in an open condition.

FIGS. 6 and 7 depict an additional device 60 useful for dispensing the copper ion treatments. The device 60 is particularly advantageous for dispensing copper ion lotions. The device 60 comprises a container or bottle 62 for holding the copper ion treatment and having a cap 64 disposed on an open end or neck of the bottle. The cap 64 could be removable or non-removable. The top surface of the cap 64 is formed by a pivotable member or disc 65 having an outlet orifice 66 along a side edge thereof. FIG. 6 depicts the cap 64 in its closed condition wherein the pivotable member 65 is in a horizontal position relative to the cap 64 and the outlet orifice 66 is disposed within the cap 64 and is not exposed. When the pivotable member 65 is depressed downwardly toward the container 62 at a location opposite the outlet orifice 66 as shown by the arrow in FIG. 7, the cap 64 will assume the open condition shown in FIG. 7 wherein the pivotable member 65 is disposed at an angle relative to the cap 64 and the outlet orifice 66 is in an exposed position located slightly above the cap 64. In use, the pivotable member 65 would be depressed using pressure applied with one or more fingers of the hand. With the cap 64 in the open condition as shown in FIG. 7, the container 62 can be squeezed manually to dispense the copper ion treatment therein from the outlet orifice 66. The cap 64 is returned to the dosed position by pressing downwardly on the pivotable member 65 at a location adjacent the outlet orifice. The device 60 is advantageous for dispensing the copper ion treatments onto the palm of the hand or fingers used to apply the treatment to anatomical tissue to be treated, but the device 60 could be used to dispense the copper ion treatments directly on the anatomical tissue to be treated.

Figure 8:
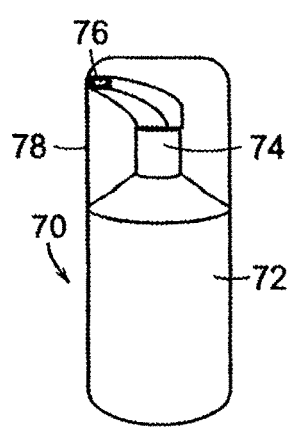
FIG. 8 is a side view of a bottle containing a copper ion treatment and having a pump nozzle for dispensing the copper ion treatment in the form of foam.

The device 70 shown in FIG. 8 is an example of a device that can be used to dispense the copper ion treatment in the form of a copper ion foam. The device 70 comprises a container 72 for holding the copper ion foam or foamable solution and having a resiliently biased foam pump dispenser 74 with an outlet orifice 76. When the foam pump dispenser 74 is depressed the full amount in a manner similar to the device 10, a predictable amount of the copper ion foam is discharged through the outlet orifice 76. If necessary, the device 70 may include a mechanism for creating foam as the copper ion treatment is discharged therefrom. The device 70 may have a removable protective cover 78 for being disposed over the foam pump dispenser 74 between uses. The device 70 could also be adapted to dispense copper ion lotions and gels.

Figure 9:
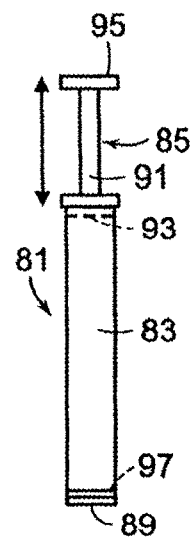
FIG. 9 is a side view of an applicator for delivering a copper ion treatment to the vagina.
Figure 10:
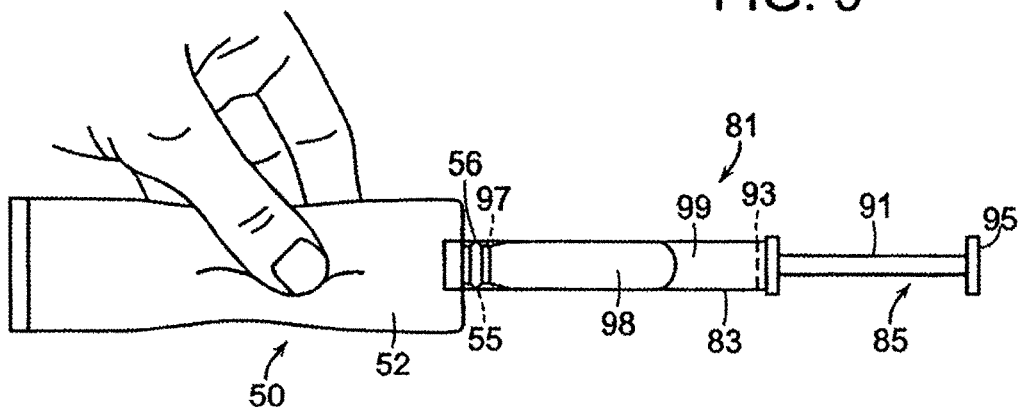
FIG. 10 is a side view of the applicator of FIG. 9 showing use of the applicator in conjunction with the tube of FIG. 5.

FIG. 9 depicts a vaginal applicator 81 useful for delivering the copper ion treatments to the vagina. The vaginal applicator 81 is particularly useful in conjunction with the device 50 as depicted in FIG. 10. Also, the vaginal applicator 81 is particularly well suited for use when the copper ion treatments are in the form of either lotion, cream or gel. The vaginal applicator 81 comprises a hollow barrel 83 and a plunger 85 slidably mounted in the hollow barrel 83. The barrel 83 has an open forward end defining a discharge opening 89 and has a rearward end wall through which a stem 91 of the plunger passes. The stem 91 is attached at one end thereof to an internal flange 93 disposed within the barrel in close, sealing relation therewith. The plunger has a finger flange 95 attached to an opposite end of the stem 91 that is disposed external of the barrel 83, the flange 95 being engageable with a finger or fingers of a hand in order to selectively depress and withdraw the plunger 85 relative to the barrel 83. For use with the device 50, the forward end of the barrel 83 is provided with an internal thread 97 to threadedly engage with the external thread 55 on the neck 56 of the tube 52.

FIG. 10 illustrates the vaginal applicator 81 being filled with the copper ion treatment from the tube 52 of the device 50. As seen in FIG. 10, the cap 54 is removed from the neck 56 of the tube 52, and the forward end of the barrel 83 is threaded onto the neck 56 via threaded engagement of the threads 55 and 97. At this stage, the plunger 85 is fully withdrawn relative to the barrel 83 such that the Internal flange 93 is in abutment with the rearward end well of the barrel 83. The tube 52 is then squeezed using pressure from the fingers in order to dispense the copper ion treatment, represented at 98, into the barrel 83 from the open neck 56 of the tube 52. When the barrel 83 is sized for a particular dosage of copper ion treatment, a sufficient amount of copper ion treatment can be dispensed from the tube 52 to entirely fill the space within the barrel 83 from the neck of the tube 56 to the internal flange 93 which is in abutment with the rearward end wall of the barrel. Alternatively, an indicia or other marking 99 can be provided on the barrel 83 to indicate the point to which the barrel 83 should be filled with copper ion treatment 98 from the tube 52. It is preferred that filling the space within the barrel from the neck of the tube to the internal flange corresponds to a dose of 5 grams of the copper ion treatment. Once the barrel 83 has been filed with the appropriate amount of copper ion treatment 98, the barrel 83 is disengaged from the neck 56 of the tube 52 by disengaging the thread 97 from the thread 55. In order to dispense the copper ion treatment 98 from the applicator 81, the finger flange 95 of the plunger 85 is depressed toward the barrel 83 using a finger, thereby causing the internal flange 93 to push the copper ion treatment 98 through the discharge opening 89 as the plunger 85 is depressed relative to the barrel 83. When the finger flange 95 meets the rearward end wall of the barrel 83, the copper ion treatment 98 will be fully discharged from the applicator. It should be appreciated that the applicator 81 could be used in conjunction with other devices for supplying the copper ion treatments to the barrel 85. It should also be appreciated that the applicator 81 can be supplied for use pre-filled with copper ion treatment 98, in which case the forward end of the barrel would be provided with a removable cap or seal. The applicator 81 is particularly advantageous for supplying the copper ion treatments to the vagina. Accordingly, prior to depressing the plunger 85 to discharge the copper ion treatment 98 from the barrel 83, the forward end of the barrel 83 would be introduced into the vagina until the rearward end of the barrel was located near the entrance to the vagina. Then, upon depressing the plunger 85, the copper ion treatment 98 is discharged from the discharge opening 89 into the vagina.

Figure 11:
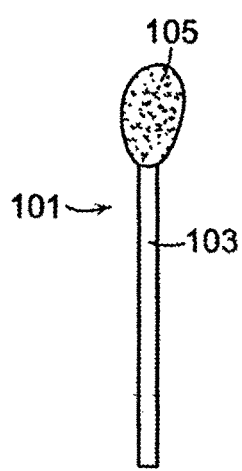
FIG. 11 is a side view of an alternative applicator for applying a copper ion treatment onto anatomical tissue.

Another type of applicator useful in applying the copper ion treatments to anatomical tissue is shown at 101 in FIG. 11. The applicator 101 is in the nature of a swab comprising a handle 103 and a body of absorbent material 105 at an end of the handle 103. The applicator 101 can be used in conjunction with a container or bottle containing a copper ion treatment, such as the device 40 of FIG. 4. Upon removal of the cap 44 from the bottle 42 of the device 40, the handle 103 of the applicator 101 can be grasped with a hand used to manipulate the applicator 101 in order to dip the body of absorbent material 105 into the copper ion treatment within the bottle 42. The body of absorbent material 105 can then be gently contacted with anatomical tissue to be treated thereby causing the copper ion treatment carried by the absorbent body 105 to be deposited on the anatomical tissue to be treated. The applicator 101 is best suited for applying copper ion treatments to localized areas of the skin, nails, ear canal, nostrils, mouth and throat. Of course, it should be appreciated that swab applicators 101 can be provided in sealed packages with the bodies of absorbent material 105 pre-supplied with copper ion treatment.

Another type of carrier that can be used to deliver copper ion treatments to the vagina is a tampon. The tampon used can be a commercially available tampon or one similar thereto. The tampon can be one having an applicator including a barrel containing the absorbent tampon body and a plunger slidable within the barrel to dispose or eject the absorbent tampon body from an open forward end of the barrel once the forward end has been introduced in the vagina an appropriate distance in a commonly known manner of tampon use. In this case, an appropriate amount of copper ion treatment can be supplied to the absorbent tampon body via the open forward end of the barrel prior to introduction of the applicator in the vagina and ejection of the absorbent tampon body from the applicator into the vagina. Another suitable tampon can be one without an applicator, i.e. a digital tampon, where the absorbent tampon body is inserted in the vagina by pushing it with the fingers. In this case, the appropriate amount of copper ion treatment is simply deposited on the absorbent tampon body prior to its insertion in the vagina. In both cases, unless the tampon is going to be inserted in the vagina immediately or soon after the absorbent tampon body has been provided with the appropriate amount of copper ion treatment, the tampon should be stored in a sealed container or package until the time of its use in order to avoid evaporation of the copper ion treatment. It should be appreciated that tampon bodies to which the copper ion treatment has been supplied can be provided in sealed containers or packages, with or without an applicator, as a ready-to-use commercial product. Alternatively, the appropriate amount of copper ion treatment may be deposited by the user on the absorbent tampon bodies of tampons sold separately or in conjunction with the copper ion treatment. Preferably, the tampon bodies are supplied with an amount of copper ion-containing solution in the range of 5 to 10 milliliters.

Figure 12:
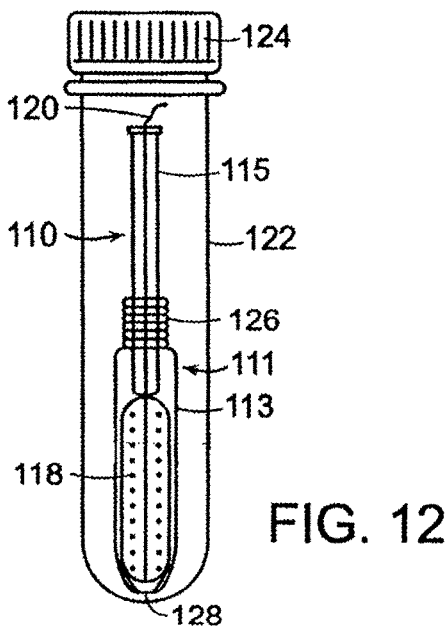
FIG. 12 is a side view of a tampon having a tampon body used as a carrier to deliver a copper ion treatment to the vagina.

FIG. 12 illustrates a tampon 110 according to an aspect of the present disclosure including an applicator 111 having a hollow barrel 113 and a hollow plunger 115, and an absorbent tampon body 118, to which the appropriate amount of copper ion treatment has been supplied, disposed in the barrel 113 with the string 120 of the tampon body extending from a rear end of the plunger 115. The plunger 115 is slidable within and toward the banal 113 to push the tampon body 118 and eject it from an open forward end 128 of the barrel. The forward end 128 of the barrel 113 can be tapered to facilitate introduction and advancement in the vagina and can be provided with slits that expand as the tampon body 118 passes therethrough. The tampon 110 is provided in an air-tight container or bottle 122 having a removable cap or lid 124. In order to use the tampon 110, the lid 124 is removed from the bottle 122 and the tampon 110 is removed from the bottle. The tampon 110 is inserted in the vagina in a conventional manner of using tampons. More specifically, the applicator 111 is held by grasping a finger grip 126 on the barrel 113, and the forward end 128 of the barrel is inserted in the vagina. The applicator 111 is advanced into the vagina until the fingers grasping the finger grip 126 touch the entrance to the vagina. The plunger 115 is then pushed into the barrel 113, thus causing the tampon body 118 to be ejected from the forward end 128 of the barrel into the vagina. The applicator 111 is then withdrawn from the vagina and discarded, leaving the tampon body 118 in place in the vagina. Once the tampon body 118 is in place in the vagina, the copper ion treatment carried by the tampon body contacts the anatomical tissue of the vagina and leaks into the vaginal fluid normally present in the vagina. The tampon body 118 is removed from the vagina at the appropriate time by grasping and pulling on the string 120. Examples of tampons according to an aspect of the present disclosure are described below in Examples 23 and 24.

Example 23

A tampon for delivering a copper ion treatment to the vagina is prepared by supplying 5 milliliters of a copper ion-containing solution to an absorbent tampon body intended to be introduced into the vagina.

Example 24

A tampon for delivering a copper ion treatment to the vagina is prepared by supplying 10 milliliters of a copper ion-containing solution to an absorbent tampon body intended to be introduced into the vagina.

The copper ion-containing solution used in Examples 23 and 24 is the copper ion-containing solution in its original form as obtained in accordance with the method set forth in Example 1. However, it should be appreciated that tampons can be provided in which the tampon bodies are supplied with the alternative copper ion-containing solutions or other forms of the copper ion treatments.

Another type of carrier useful to deliver the copper ion treatments to the vagina and rectum is a suppository. Suppositories are commonly used in the vagina and rectum (anus) as a means for dispensing various active ingredients or medicaments. Suppositories are made in various shapes including oviform, globular, conical and bullet shapes, and in various sizes. Suppositories typically weigh in the range of 1 to 5 grams. Suppositories can be solid bodies composed of a mixture of a suitable suppository base material and the active ingredients or medicaments. Alternatively, suppositories can be made with a solid outer wall of suppository base material enclosing non-solid active ingredients or medicaments. The suppository base materials used in suppositories allow them to dissolve or melt when exposed to the moisture (body fluid) or heat (body temperature) found in the vagina or rectum (rectal or anal canal), thereby releasing the active ingredients or medicaments into the vagina or rectum. Suitable suppository base materials include oleaginous (fatty) base materials, including cocoa butter, theobroma oil and synthetic triglycerides, or water soluble or miscible base materials, including glycerinated gelatin and polyethylene glycol (PEG) polymers. It is preferred that the base materials be non-toxic, non-irritating, inert, and biocompatible. Suppositories suitable for use in an aspect of the present disclosure can be prepared in various ways according to conventional methods for preparing suppositories including compression molding and fusion molding. Suppositories for use as vaginal and rectal suppositories according to an aspect of the present disclosure are preferably made in two different sizes, i.e. a suppository weighing 3 grams and a suppository weighing 5 grams, to accommodate different sizes of vaginal and rectal anatomy. Each size suppository can be made in different strengths based on the percentage by weight of the active ingredient. i.e. the copper ion treatment, relative to the total weight of the suppository. Preferably, the amount of copper ion-containing solution in the suppository is in the range of 5% to 30% of the total weight of the suppository. The suppositories are preferably formed in plastic molds and can be stored at room temperature. The suppositories will be effective against the body condition being treated when the only active ingredient contained in the vaginal and rectal suppositories is the copper ion treatment. However, the vaginal and rectal suppositories could contain additional ingredients that are inactive with respect to the underlying condition or conditions being treated, such as preservatives, penetrating additives, bioadhesives and stability aids. The suppositories may be inserted in the vagina and rectum using the fingers, or the suppositories may be provided with applicators to facilitate insertion thereof in the vagina and rectum. Examples of vaginal and rectal suppositories according to an aspect of the present disclosure are set forth in Examples 25-32, which utilize the copper ion-containing solution of Example 1. However, the alternative copper ion-containing solutions could be used in Examples 25-32.

Example 25

A suppository base material is combined with an appropriate amount of copper ion-containing solution and is molded into a suppository for vaginal or rectal use having a total weight of 3 grams, wherein the copper ion-containing solution constitutes 5 percent of the total weight of the suppository.

Example 26

A suppository base material is combined with an appropriate amount of copper ion-containing solution and is molded into a suppository for vaginal or rectal use having a total weight of 3 grams, wherein the copper ion-containing solution constitutes 10 percent of the total weight of the suppository.

Example 27

A suppository base material is combined with an appropriate amount of copper ion-containing solution and is molded into a suppository for vaginal or rectal use having a total weight of 3 grams, wherein the copper ion-containing solution constitutes 20 percent of the total weight of the suppository.

Example 28

A suppository base material is combined with an appropriate amount of copper ion-containing solution and is molded into a suppository for vaginal or rectal use having a total weight of 3 grams, wherein the copper ion-containing solution constitutes 30 percent of the total weight of the suppository.

Example 29

A suppository base material is combined with an appropriate amount of copper ion-containing solution and is molded into a suppository for vaginal or rectal use having a total weight of 5 grams, wherein the copper ion-containing solution constitutes 5 percent of the total weight of the suppository.

Example 30

A suppository base material is combined with an appropriate amount of copper ion-containing solution and is molded into a suppository for vaginal or rectal use having a total weight of 5 grams, wherein the copper ion-containing solution constitutes 10 percent of the total weight of the suppository.

Example 31

A suppository base material is combined with an appropriate amount of copper ion-containing solution and is molded into a suppository for vaginal or rectal use having a total weight of 5 grams, wherein the copper ion-containing solution constitutes 20 percent of the total weight of the suppository.

Example 32

A suppository base material is combined with an appropriate amount of copper ion-containing solution and is molded into a suppository for vaginal or rectal use having a total weight of 5 grams, wherein the copper ion-containing solution constitutes 30 percent of the total weight of the suppository.

Figure 13:
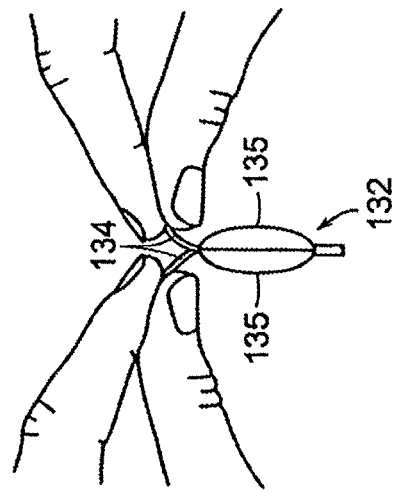
FIG. 13 is a broken front view of a plurality of suppositories containing a copper ion treatment, the suppositories being insertable in the vagina or rectum to deliver the copper ion treatment to the vagina or rectum.
Figure 14:
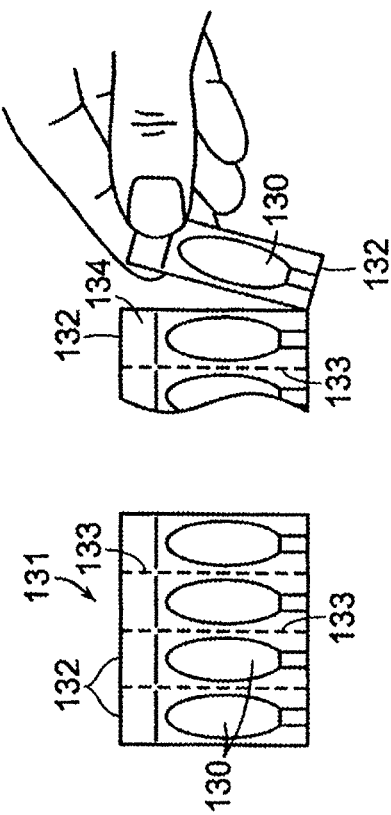
FIG. 14 is a side view showing a suppository of FIG. 13 being removed from its package.

FIG. 13 illustrates a strip 131 of interconnected packages or pods 132, each enclosing a vaginal or rectal suppository 130 containing a copper ion treatment. The pods 132 are separated from each other by a perforation line 133 allowing the pods 132 to be detached from each other by tearing along the perforation lines 133 as depicted in FIG. 13. Each pod 132 has front and rear walls 135 between which a suppository 130 is retained. The front and rear walls 135 are sealed to one another along their peripheral edges. As shown in FIG. 14, each pod 132 is provided with a pair of finger tabs 134 respectively attached to the front and rear walls 135, the finger tabs 134 being capable of being pulled in opposite directions using the fingers to separate the opposed walls 135 and thereby release the suppository 130 contained therein.

Figure 15:
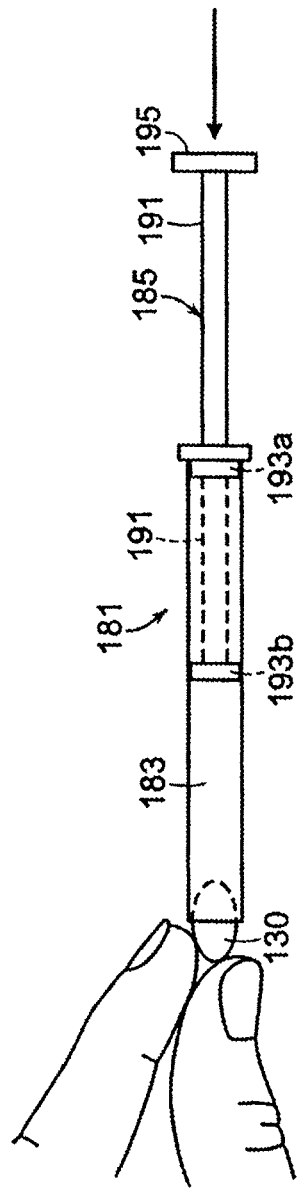
FIG. 15 is a side view of an applicator for delivering the suppositories of FIG. 13 to the vagina or rectum.

FIG. 15 illustrates an applicator 181 suitable for use in delivering a suppository 130 to the vagina or rectum. The applicator 181 is similar to the applicator 81 but does not have an internal thread at the forward end of the barrel 183. In addition, the plunger 186 of the applicator 181 has two internal flanges 193a and 193b within the barrel 183, the flange 193a controlling the distance that the plunger can be withdrawn relative to the barrel and the flange 193b serving to eject the suppository from the barrel when the plunger is depressed the full amount. In use, a suppository 130 is manually positioned in the open forward end of the barrel 183 as illustrated in FIG. 15. The open forward end of the barrel 183 is preferably sized to retain the suppository 130 in position without being overly snug or tight. The plunger 185 is withdrawn the full amount relative to the barrel 183, which coincides with abutment of internal flange 193a with the rearward end wall of the barrel 183. The forward end of the barrel 183 holding the suppository is then introduced in the vagina or rectal (anal) canal, and the applicator 181 is gently pushed into the vagina or rectal canal until the fingers holding the rearward end of the barrel 183 are adjacent or touch the entrance to the vagina or rectal canal. The finger flange 195 is then depressed to push the plunger 185 toward and into the barrel 183 as shown by the arrow in FIG. 15, thus causing the flange 193b to engage the suppository 130 and eject it from the forward end of the barrel into the vagina or rectal canal. The applicator 181 is then removed from the vagina or rectal canal, leaving the suppository in the vagina or rectal canal. The suppository will melt or dissolve in the vagina or rectal canal such that the copper ion treatment is released to contact anatomical tissue of the vagina or rectal canal and to mingle with body fluid present in the vagina or rectal canal.

Figure 16:
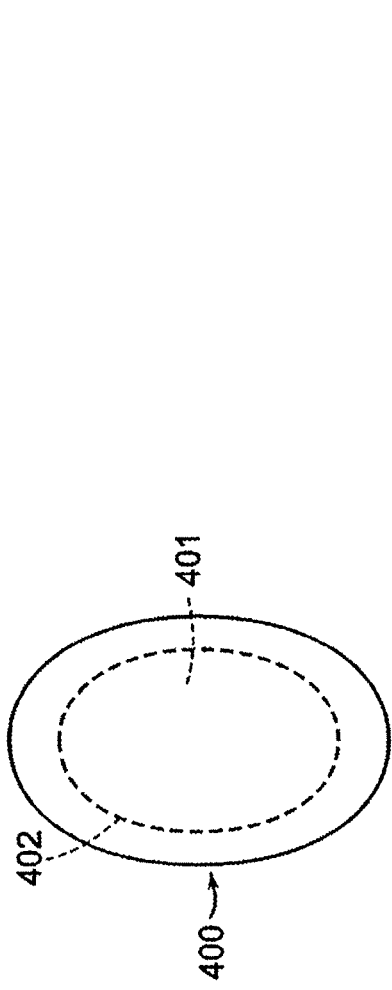
FIG. 16 is a front view of a package containing a body wipe carrying a copper ion treatment and showing the package partially open to remove the body wipe therefrom.

Another type of carrier that can be used to deliver the copper ion treatments to anatomical tissue is a body wipe. FIG. 16 illustrates a body wipe 200 contained in a sealed package 202 having front and rear walls 203. The body wipe 200 comprises a thin sheet of material disposed in a folded condition when retained between the front and rear walls 203, which are sealed along their peripheral edges. The body wipe 200 enclosed between the front and rear walls 203 contains a wet or moist copper ion treatment. The front and rear walls 203 may be grasped by the fingers at corresponding corners thereof and pulled in opposite directions similar to the pods 132 in order to separate the front and rear walls 203 and thereby allow the body wipe 200 to be removed from the package 202. FIG. 16 shows the package 202 in a partially open condition in which corresponding corner sections of the front and rear walls 203 have been peeled away from one another thereby providing access to the body wipe 200. Upon removal from the package 202, the body wipe 200 can be unfolded to its full size, which is substantially larger than its size in the folded condition, and can be used to wipe anatomical tissue to be treated causing the copper ion treatment to be transferred to the anatomical tissue. The body wipe 200 is advantageous for applying the copper ion treatments to the skin and the external genital and rectal areas.

Figure 17:
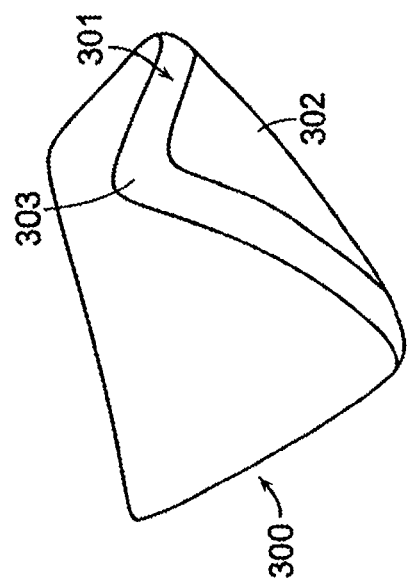
FIG. 17 is a perspective view of a wound dressing supplied with a copper ion treatment.

Another type of carrier for the copper ion treatments is a wound dressing, such as a band aid, gauze pad or similar device. Such carriers can be selected from products that are commercially available for removable application to the skin to temporarily cover and protect an affected area of the skin. FIG. 17 depicts a carrier in the nature of a wound dressing 300 having a surface 301 for being placed in contact with the skin. The surface 301 includes a protective surface 302 for being positioned over a wound, and an adhesive border surrounding the surface 302. In use, a copper ion treatment, such as the copper ion-containing solution in original form, can be liberally sprayed onto the surface 302 of the carrier that is applied adjacent or in contact with the skin. Then, when the surface 302 of the carrier is applied adjacent or in contact with the skin and the carrier is left in place on the skin for a period of time, the copper ions contact or are transferred to the skin and provide the therapeutic effects described above. Of course, it would be possible to provide carriers of this type in sealed packages in which the carriers are pre-supplied or pre-treated with the copper ion treatment similar to the body wipe 200.

Figure 18:
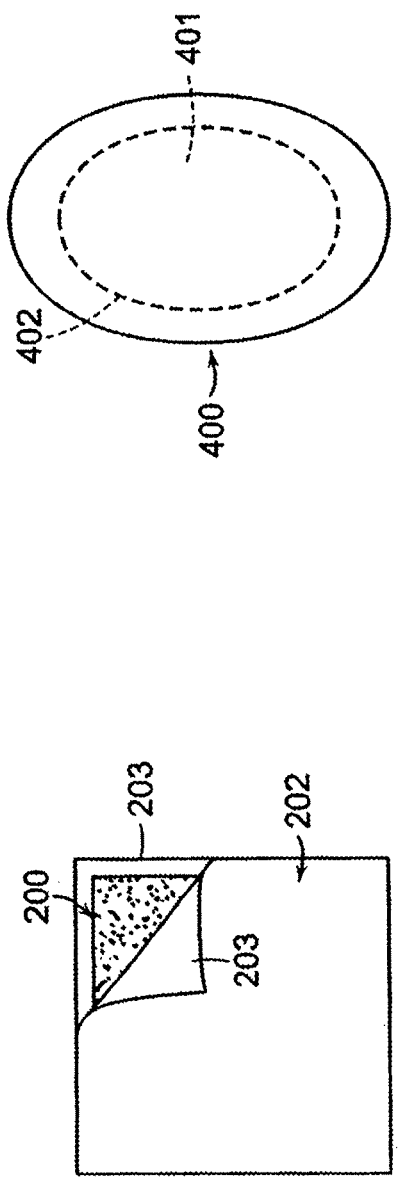
FIG. 18 is a plan view of a skin patch carrying a copper ion treatment.

A further type of carrier for the copper ion treatments is a skin patch, such as a dermal patch or a transdermal patch, represented at 400 in FIG. 18. The skin patch 400 has a drug delivery surface 401 containing the copper ion treatment surrounded by an adhesive border 402. The patch is applied to the skin and left in place for a period of time with the drug delivery surface in contact with the skin, causing the copper ions to diffuse through the skin where they can act locally or penetrate the capillaries for broader systemic effects. Examples of suitable transdermal patches are the transdermal and microneedle 3M Drug Delivery Systems manufactured by 3M Corporation.

Figure 19:
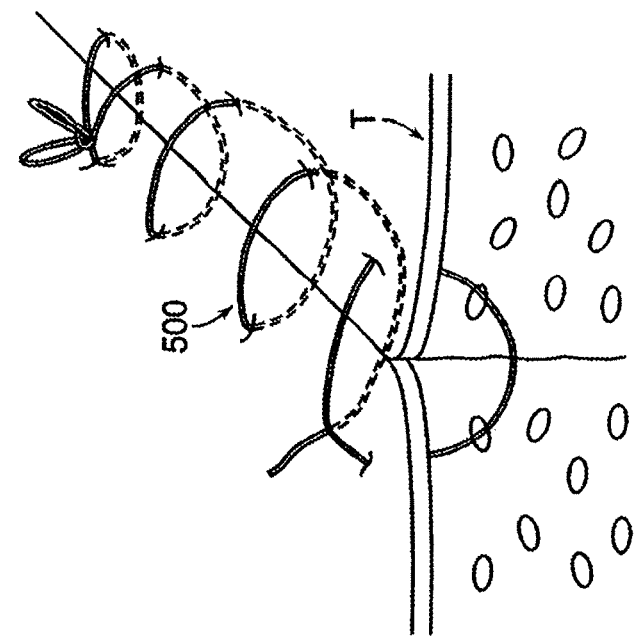
FIG. 19 is a perspective view of sutures created in anatomical tissue using suture material carrying a copper ion treatment.

An additional type of carrier for the copper ion treatments is suture material, represented at 500 in FIG. 19, used by medical professionals to close or suture external or internal incisions or wounds, i.e. "stitches." Prior to using the suture material 500, which can be conventional suture material, the suture material can be soaked in the copper ion-containing solution for a period of time in order to cover or saturate the suture material with the solution. Suture material can also be stored in sealed packages containing the copper ion-containing solution. Then, when the suture material 500 is used to create sutures or stitches in anatomical tissue T as seen in FIG. 19, the copper ions in the solution contact the anatomical tissue and provide the therapeutic effects previously described.

The copper ion-containing solution and the other forms of copper ion treatments described herein can be used on anatomical tissue in various areas of the body including the genital-rectal areas (vagina, vulva, penis, scrotum, rectum (anus), rectal (anal) canal and surrounding anatomical areas), the oral-respiratory-otic areas (mouth, throat, airway, nostrils and ears) and the dermatological areas (skin and nails) of the body. The treatment effects provided by the copper ion treatments encompass treatment of active or existing disease and other undesirable body conditions as well as the prevention of such diseases and conditions. The copper ion treatments are especially beneficial for their ability to kill or neutralize harmful or undesired pathogens and microbes including bacteria, viruses and fungi.

Although the copper ion treatments am applied topically to anatomical tissue and have a localized effect on diseases and undesirable body conditions affecting the anatomical tissue, the copper ion treatments also have a broader systemic effect on diseases and undesirable body conditions. The effects realized with the copper ion treatments include antibacterial, antimicrobial, antiseptic, antifungal, antiviral, anti-pathogenic, anti-inflammatory, spermicidal, neutralization of free radicals, promotion of healing and tissue repair, prevention of biofilm, and immune-boosting effects. The diseases or conditions affecting the genital-rectal areas that are treatable with the copper ion treatments include reducing and/or preventing the symptoms of radiation damage (e.g. radiation dermatitis), vaginitis, bacterial vaginosis, hemorrhoids, vaginal dryness, imbalances in vaginal pH, bacterial infections caused by gonorrhea, chlamydia, streptococcus and staphylococcus, protozoan infections caused by trichomonas, pelvic inflammatory disease, viral infections caused by herpes (I and II), HPV and HIV, fungal infections caused by yeast candida, thrush and other fungi, exposure to sexually transmitted diseases, and the risk of undesired pregnancy (contraception). The diseases or conditions affecting the oral-respiratory-otic areas that are treatable with the copper ion treatments include reducing and/or preventing the symptoms of radiation damage (e.g. radiation dermatitis), bacterial infections caused by gonorrhea, chlamydia, streptococcus and staphylococcus, protozoan infections caused by trichomonas, viral infections caused by herpes (I and II), HPV and HIV, canker sores, mouth sores, mouth ulcers, colds, sinusitis, rhinosinusitis, sore throat, nasal discharge, congestion, runny nose, bronchitis, allergies, asthma, tonsillitis, wheezing, sneezing, ear infections, earache, pressure in the ears, cough, hoarseness, laryngitis, sore gums, periodontal disease, bad breath and tooth decay. The diseases or conditions affecting the dermatological areas that are treatable with the copper ion treatments include reducing and/or preventing the symptoms of radiation damage (e.g. radiation dermatitis), bacterial infections caused by staphylococcus, streptococcus, enterobacter, E. coli and pseudomonas, viral infections caused by shingles and the associated postherpetic neuralgia (PUN) (a chronic, painful condition that can follow shingles), herpes (I and II) and HPV, fungal infections such as athlete's foot, ringworm and toenail fungus, impetigo, rosacea, psoriasis, eczema, warts, sun/wind damage (including sun burns, a form of radiation damage), dry skin, age spots, pigmentation, scarring, blisters, boils, cysts, pimples, cuts, scratches, burns, abrasions, splinters, insect bites and stings, animal bites and scratches, ulcers, loss of elasticity or collagen, wrinkles, sagging skin, acne, measles, chicken pox, and the presence of pathogens and microbes on the skin that is an inevitable consequence of daily life. Based on the result of laboratory testing, it is expected that the copper ion treatments will kill bacteria causing bacterial vaginosis, gonorrhea and chlamydia, and the viruses responsible for herpes (I and II) and HIV at a kill rate of 99.99 percent in 6 hours. Accordingly, the copper ion treatments are sufficiently effective to "cure" the diseases and conditions described herein and to prevent the occurrence or development of such diseases and conditions. Similarly, copper has been demonstrated as having the capability to kill or render inactive staphylococcus, streptococcus, enterobacter, trichomonas, E. coli and pseudomonas. The copper ion treatments are highly effective at treating the various abnormal or undesired body conditions while being safe and non-toxic. In particular, copper toxicity is so rare that the World Health Organization (WHO) has determined that there is no need for setting an upper threshold for the ingestion of copper. The copper ion treatments can thus be safely used without concern for overdosing or improper use. Moreover, it is believed that, to date, no bacteria or other harmful microorganisms have been found to be capable of developing a resistance to copper, in contrast to the many bacteria and organisms that have developed or are in the process of developing resistance to conventional antibiotics. The multi-target effects of copper makes bacterial resistance extremely unlikely as copper kills bacteria very quickly and leaves almost no survivors. Consequently, there is neither the time for bacteria to "learn" how to resist the killing effect of copper or the possibility to pass on any knowledge to a significant population of survivors. The copper ion treatments provide a degree of efficacy and safety for treating a wide array of diseases and body conditions that far surpasses conventional pharmaceutical and non-pharmaceutical products and drugs available for treating the same conditions.

Example 33

Treatment of Osteoarthritis Associated Chronic Pain with 3VM1001 Cream

Studies related to the palliative and therapeutic effects of the instant technology were performed with respect to osteoarthritic pain. Similar treatments, compositions, and methods are envisioned as being effective in reducing and/or preventing the symptoms of radiation damage (e.g. radiation dermatitis).

Study Design

This study was a double-blind, placebo-controlled, randomized study of the use of 2 g of 3VM1001 cream, applied thrice daily, for the treatment of chronic pain associated with osteoarthritis of the knee compared to the inactive vehicle as a placebo. The composition of 3VM1001 cream is provided in Example 34. Subjects were randomized in a 1:1 ratio to one of two treatment arms (a) treatment with 3VM1001 cream or (b) placebo (3VM1002). A total of 50 subjects were enrolled, out of which 40 subjects were evaluable.

The treatment phase consisted of a total of 90 self-administered treatments for chronic pain with either 3VM1001 cream or placebo. All subjects were to have three (3) study visits: an initial Screening/Entry (Visit 1) which may have taken place on two days over a period of seven days to allow for a knee radiograph to be taken and reviewed, a follow up visit at Day 7 after commencement of treatment (Visit 2) and a final visit (Visit 3) at 30 days after the commencement of treatment. Visits 2 and 3 may take place ±3 days from the due date.

The results from one of the two study sites are summarized below.

Statistical Methods

The primary efficacy endpoint was the change from baseline in the time-averaged self-reported Visual Analog Scale (VAS) score. Secondary endpoints included the following:
1. Change from baseline in the (VAS) score at Visits 2 and 3.
2. Change from baseline in the time-averaged self-reported WOMAC (Western Ontario and McMaster Universities) Pain Subscale score.
3. The change in the Global Rating of Disease from Baseline (Day 0) to Day 30.
4. The Patient Global Impression of Change from Baseline in Osteoarthritis.
5. The change in Patient Global Assessment of Treatment Satisfaction from baseline to the end of the study.

6. The use of rescue medication.

The time-averaged mean change from baseline in the VAS for each subject was calculated by first computing the area under the curve (AUC) of the changes from baseline vs. study day curve using the trapezoidal rule. The AUC was then divided by the number of study days from the first to the last observation. These time-averaged means were analyzed by a one-way analysis of covariance that included the effects of treatment group and baseline VAS. Data from all study days (including those beyond 30 days) were included in the calculation of the time-averaged means. The mean changes from baseline in the daily VAS scores were created by first imputing all missing data through Day 30 by carrying the last value forward.

Change from baseline in the VAS score at Visits 2 and 3 were each analyzed by a one-way analysis of covariance that included the effects of treatment group and baseline VAS.

Change from baseline in the WOMAC Pain Subscale score at Visits 2 and 3 were each analyzed by a one-way analysis of covariance that included the effects of treatment group and baseline score. Time-averaged mean changes from baseline and daily mean graphs were done as described above for self-reported VAS scores.

The change in the Global Rating of Disease from Baseline (Day 0) to Day 30 was analyzed by the Cochran-Mantel-Haenszel procedure by assigning uniform scores (0-4) to each of the ordered outcomes of the 5-point scale, stratified by the baseline score.

The Patient Global Impression of Change from Baseline in Osteoarthritis Pain was analyzed by the Cochran-Mantel-Haenszel procedure by assigning uniform scores (0-6) to each of the ordered outcomes of the 7-point scale.

The change in Patient Global Assessment of Treatment Satisfaction from baseline to the end of the study was analyzed by the Cochran-Mantel-Haenszel procedure by assigning uniform scores (0-4) to each of the ordered outcomes of the 5-point scale.

The use of rescue medication was analyzed by counting the number of days each subject took one or more doses of rescue medication. Subjects who terminated prematurely or did not have exactly 30 diary days had their number of days with rescue medication normalized to 30 days by dividing the number of days they took a rescue medication by the number of days they had diary data and multiplying by 30. These data were analyzed by a two-sample t test.

The primary and all secondary analyses were two-sided and tested at a significance level of 5%.

Results

Table 1 summarizes demographic data for the two treatment groups. Demographically, the two groups were comparable.

TABLE 1

Demographic Summary

|  | 3VM1001 (N = 11) | Placebo (N = 12) |
|---|---|---|
| Age |  |  |
| N | 9 | 12 |
| Mean | 58.1 | 61.9 |
| Range | 49-73 | 52-74 |
| Sex |  |  |
| Males: n (%) | 6 (54.5%) | 7 (58.3%) |
| Females: n (%) | 5 (45.5%) | 5 (41.7%) |

TABLE 1-continued

Demographic Summary

|  | 3VM1001 (N = 11) | Placebo (N = 12) |
|---|---|---|
| Race |  |  |
| Black: n (%) | 6 (54.5%) | 4 (33.3%) |
| Caucasian: n (%) | 5 (45.5%) | 8 (66.7%) |

Table 2 summarizes the time-averaged changes from baseline I the VAS and the WOMAC scores. Mean improvements over placebo were 16.2 and 3.1 for the VAS and WOMAC, respectively.

TABLE 2

Mean Time-Averaged Changes From Baseline in Daily Diary Scores

|  | VAS | | WOMAC Total | |
|---|---|---|---|---|
|  | 3VM1001 | Placebo | 3VM1001 | Placebo |
| Baseline Mean Changes | 69.6 | 65.6 | 16.4 | 16.4 |
| N | 10 | 12 | 10 | 12 |
| Mean[1] | −26.1 | −9.9 | −4.47 | −1.37 |
| Difference (95% CI) | −16.2 (−36.6 to 4.2) | | −3.10 (−6.48 to 0.28) | |
| P-Value | 0.113 | | 0.011 | |

[1]Adjusted for baseline

Figure 20:
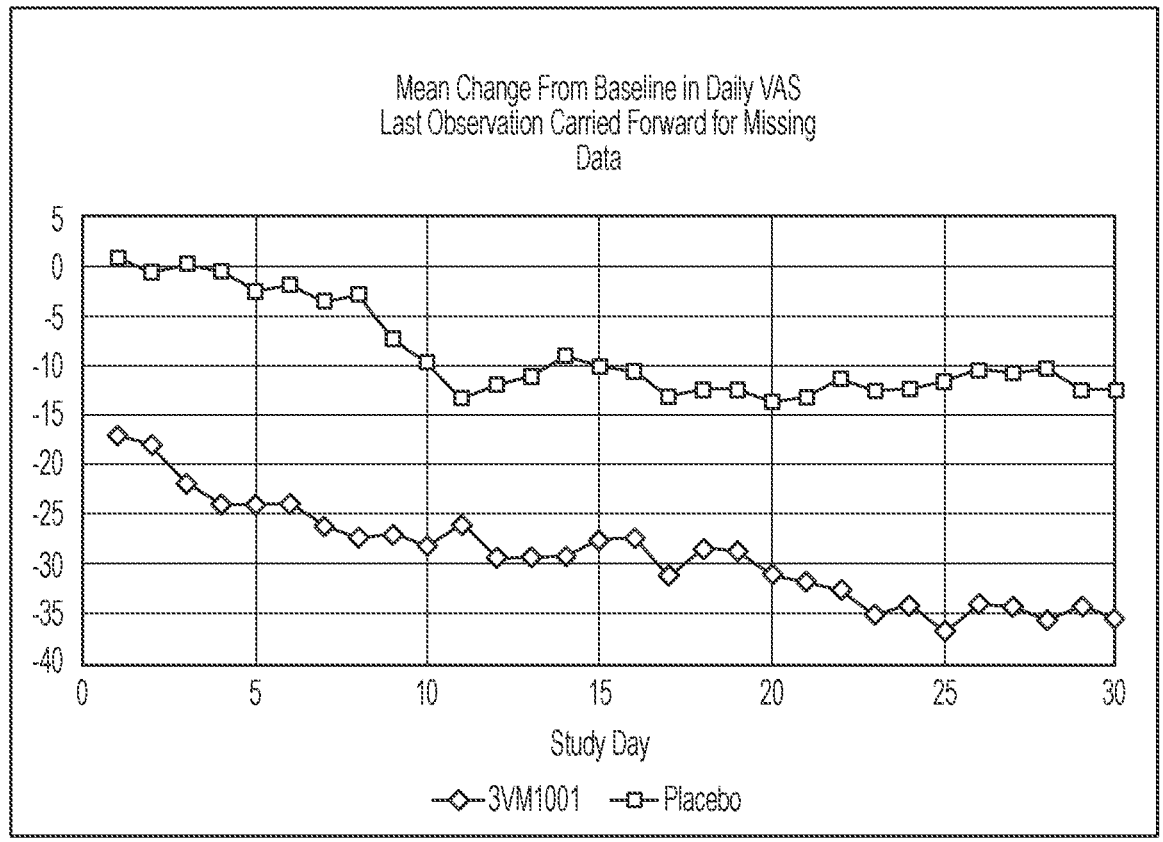
FIG. 20 shows the mean change from baseline in daily VAS for osteoarthritis patients treated with 3VM1001.
Figure 21:
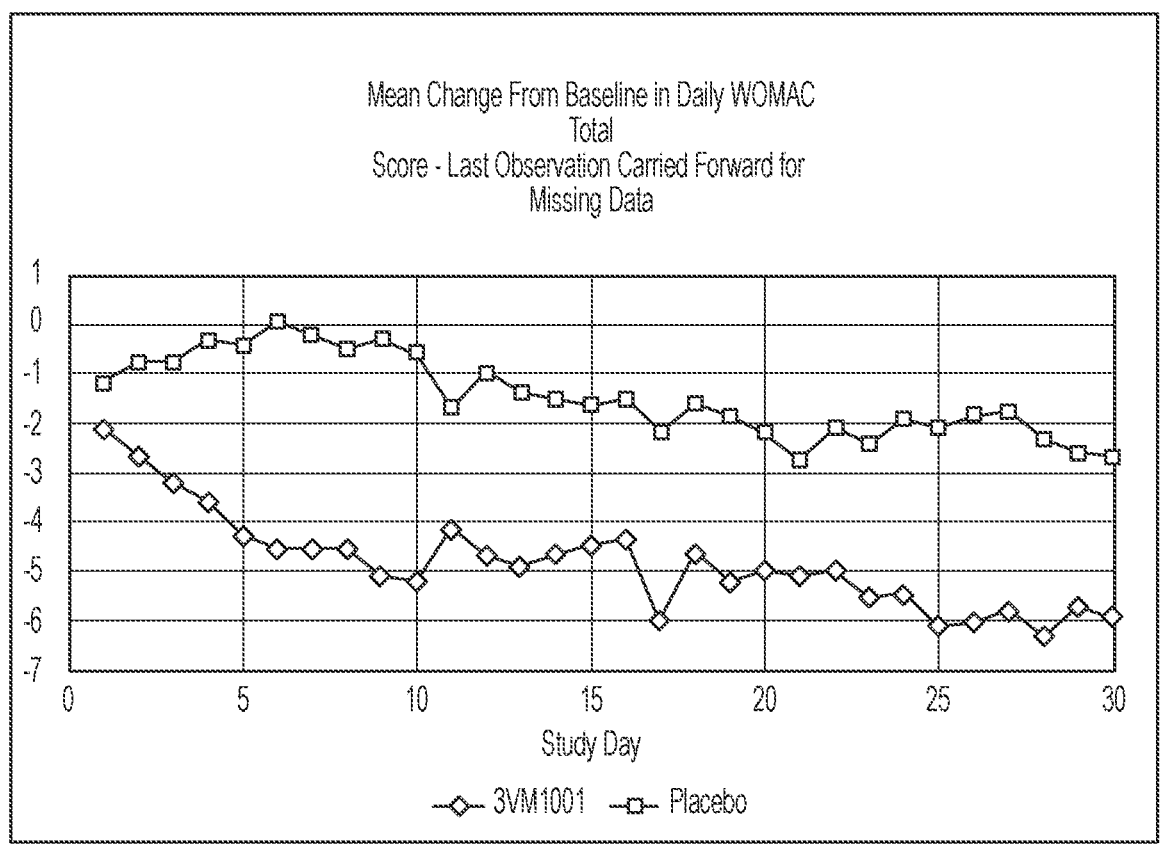
FIG. 21 shows the mean change from baseline in daily WOMAC score for osteoarthritis patients treated with 3VM1001.

Mean changes from baseline over time for the VAS and WOMAC are shown in FIGS. 20 and 21, respectively. Trends favoring 3VM1001 are seen throughout the entire 30 days of treatment.

Table 3 summarizes the changes from baseline in the VAS scores at Days 7 and 30. Mean improvements over placebo were 22.8 and 13.1 at Days 7 and 30, respectively.

TABLE 3

VAS Scores at Days 7 and 30

|  | Day 7 | | Day 30 | |
|---|---|---|---|---|
|  | 3VM1001 | Placebo | 3VM1001 | Placebo |
| Baseline Mean Changes | 67.8 | 65.6 | 69.6 | 65.6 |
| N | 11 | 12 | 10 | 12 |
| Mean[1] | −28.6 | −5.8 | −31.0 | −17.9 |
| Difference (95% CI) | −22.8 (−45.1 to −0.6) | | −13.1 (−36.0 to 9.7) | |
| P-Value | 0.045 | | 0.24 | |

[1]Adjusted for baseline

Table 4 summarizes the changes from baseline in the WOMAC scores at Days 7 and 30. Mean improvements over placebo were 5.4 and 2.4 at Days 7 and 30, respectively.

TABLE 4

WOMAC Total Scores at Day 7 and 30

|  | Day 7 | | Day 30 | |
| --- | --- | --- | --- | --- |
|  | 3VM1001 | Placebo | 3VM1001 | Placebo |
| Baseline Mean Changes | 16.3 | 16.4 | 16.4 | 16.2 |
| N | 11 | 12 | 10 | 11 |
| Mean[1] | −5.57 | −0.14 | −5.94 | −3.51 |
| Difference (95% CI) | −5.43 (−9.27 to −1.58) | | −2.43 (−6.96 to 1.84) | |
| P-Value | 0.008 | | 0.25 | |

[1]Adjusted for baseline

Table 5 summarizes the satisfaction with the current treatment; Table 6 summarizes the improvement with treatment; and Table 7 summarizes the global rating of disease. In each, the 3VM1001 showed consistently higher scores throughout treatment.

TABLE 5

Satisfaction With Current Treatment

|  | Day 7 | | Day 30 | |
| --- | --- | --- | --- | --- |
|  | 3VM1001 | Placebo | 3VM1001 | Placebo |
| Very Dissatisfied | 0 | 0 | 0 | 0 |
| Dissatisfied | 1 | 4 | 3 | 2 |
| No Preference | 3 | 3 | 1 | 2 |
| Satisfied | 2 | 4 | 1 | 6 |
| Very Satisfied | 5 | 1 | 5 | 2 |
| P-Value | 0.075 | | 0.79 | |

TABLE 6

Improvement With Treatment

|  | Day 7 | | Day 30 | |
| --- | --- | --- | --- | --- |
|  | 3VM1001 | Placebo | 3VM1001 | Placebo |
| Very much improved | 0 | 0 | 3 | 2 |
| Much improved | 3 | 2 | 1 | 0 |
| Improved | 5 | 4 | 2 | 5 |
| No change | 3 | 4 | 4 | 4 |
| Worse | 0 | 0 | 0 | 0 |
| Much worse | 0 | 1 | 0 | 1 |
| Very much worse | 0 | 1 | 0 | 0 |
| P-Value | 0.15 | | 0.34 | |

TABLE 7

Global Rating of Disease

|  | Baseline | | Day 7 | | Day 30 | |
| --- | --- | --- | --- | --- | --- | --- |
|  | 3VM1001 | Placebo | 3VM1001 | Placebo | 3VM1001 | Placebo |
| Excellent | 0 | 0 | 1 | 0 | 0 | 0 |
| Very good | 0 | 0 | 1 | 1 | 3 | 2 |
| Good | 1 | 0 | 2 | 0 | 4 | 2 |
| Fair | 7 | 7 | 4 | 6 | 1 | 7 |
| Poor | 4 | 5 | 3 | 5 | 2 | 1 |
| P-value |  |  | 0.32 | | 0.55 | |

Table 8 summarizes the use of rescue medication. Thirty percent of the subjects who received 3VM1001 took at least one dose of rescue medication, compared to 50% of placebo subjects.

TABLE 8

Use of Rescue Medication

|  | 3VM1001 | Placebo | P-Value |
| --- | --- | --- | --- |
| N | 10 | 12 |  |
| Subjects who took at least one dose: n (%) | 3 (30%) | 6 (50%) |  |
| Mean | 4.2 | 4.4 | 0.95[1] |
| Range | 0-26.5 | 0-22.9 |  |
| Median | 0 | 0.5 | 0.51[2] |

[1]Two sample t test
[2]Wilcoxon Rank Sum test

Table 9 summarizes adverse events. All events were rated as mild and all were rated remote or unrelated by the investigator, except for headache, which was not rated for causality. No action was taken for any adverse event, except the bacterial skin infection which appeared to be the result of a sports injury not the 3VM1001 cream, and which resulted in the patient terminating from the study.

TABLE 9

Adverse Event Summary

| Adverse Event | 3VM1001 (N = 11) n (%) | Placebo (N = 12) n (%) |
| --- | --- | --- |
| Bacterial skin infection - R knee | 1 (9.1%) | 0 (0%) |
| Cold symptoms | 0 (0%) | 1 (8.3%) |
| Headache | 0 (0%) | 1 (8.3%) |
| Minimal erythema - Left Knee | 1 (9.1%) | 0 (0%) |
| Stomach Virus | 0 (0%) | 1 (8.3%) |
| Tooth Pain | 0 (0%) | 1 (8.3%) |

Example 34

Preparation of the Copper Ion Bulk Suspension

Figure 22:
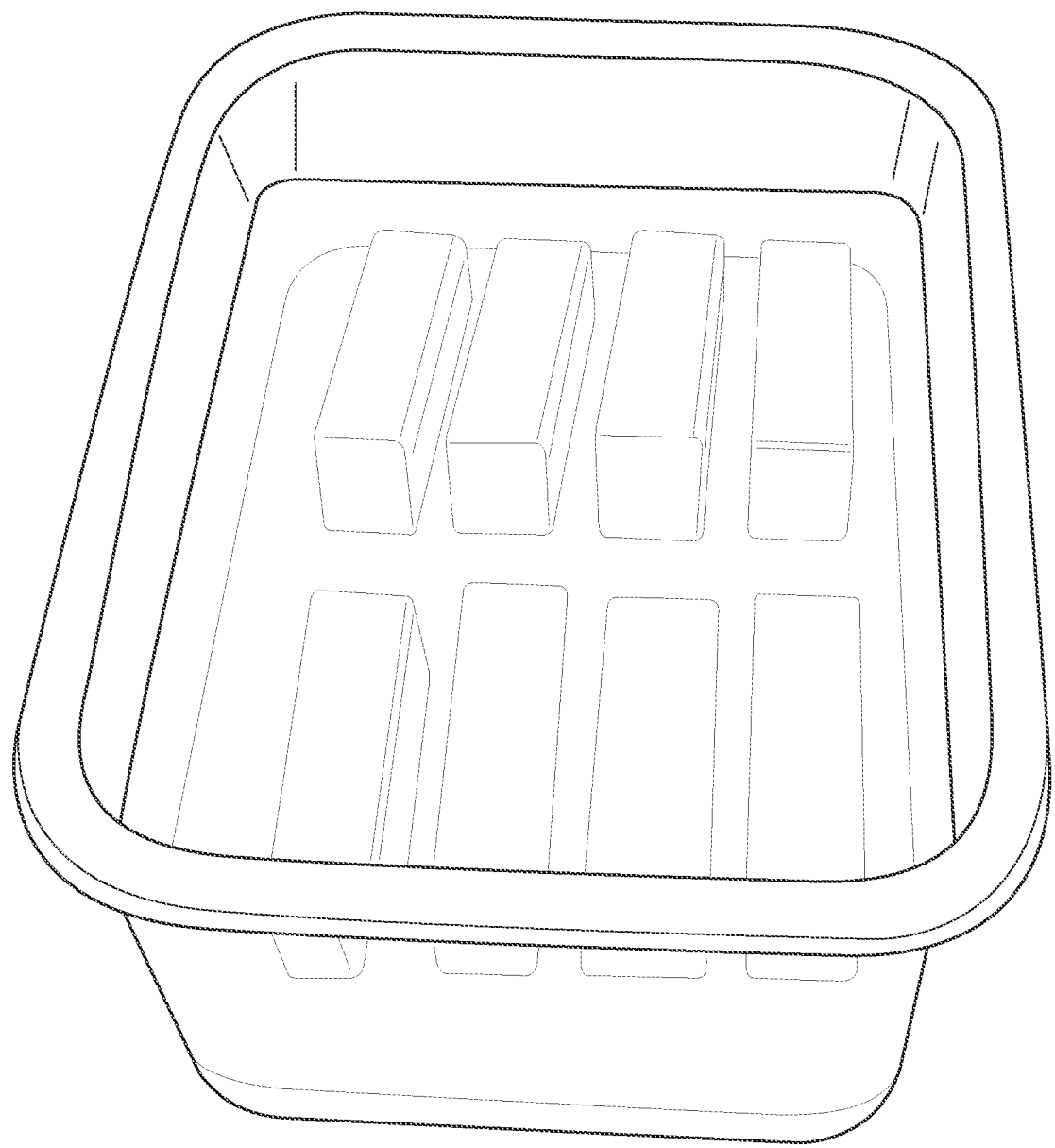
FIG. 22 shows copper strips separated by using stainless steel rods in a phosphate buffered saline solution.
Figure 23:
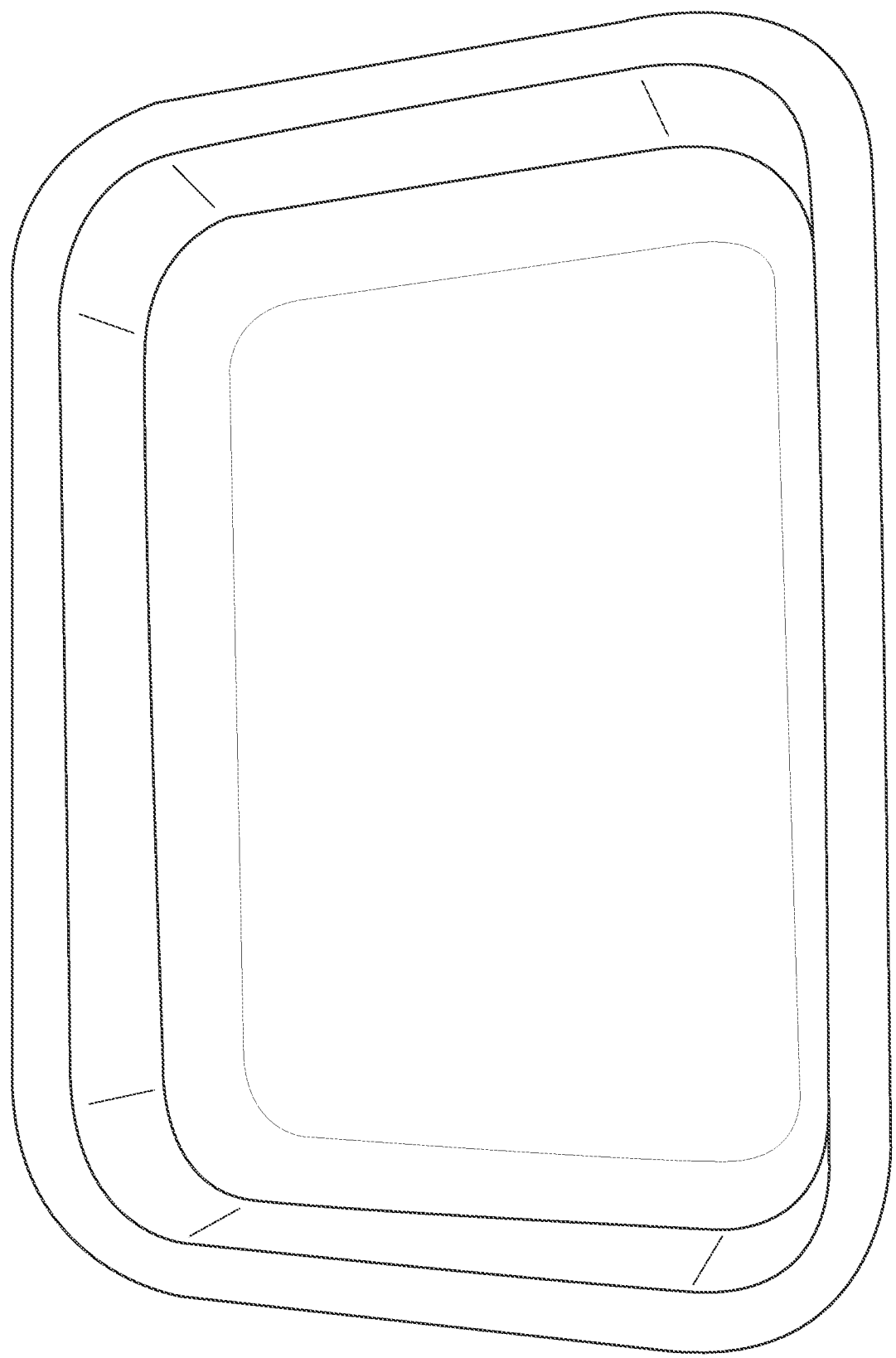
FIG. 23 shows the bulk suspension obtained after incubating phosphate buffer saline with copper strips.
Figure 24:
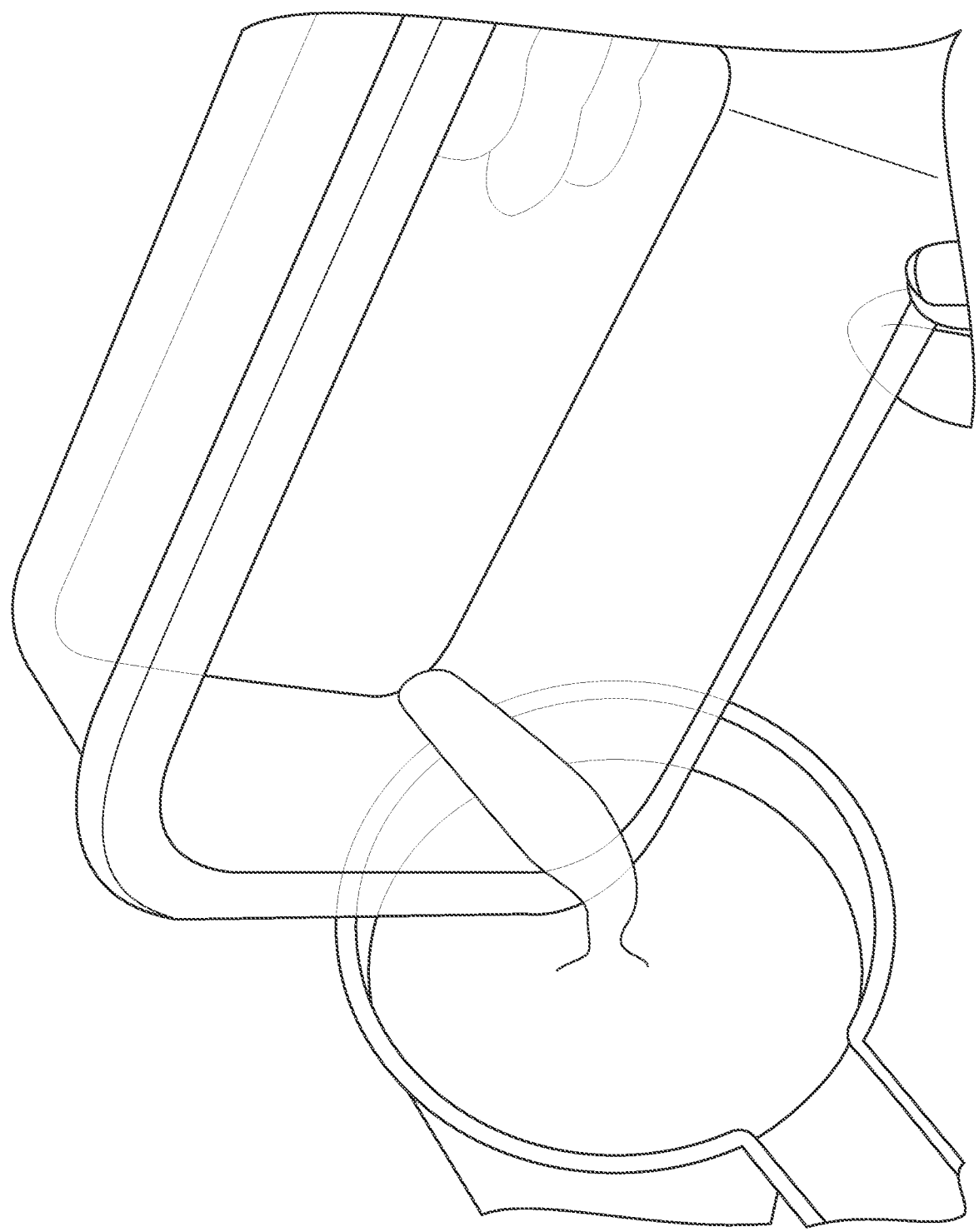
FIG. 24 shows the transfer of the bulk suspension to a measuring cup.
Figure 25:
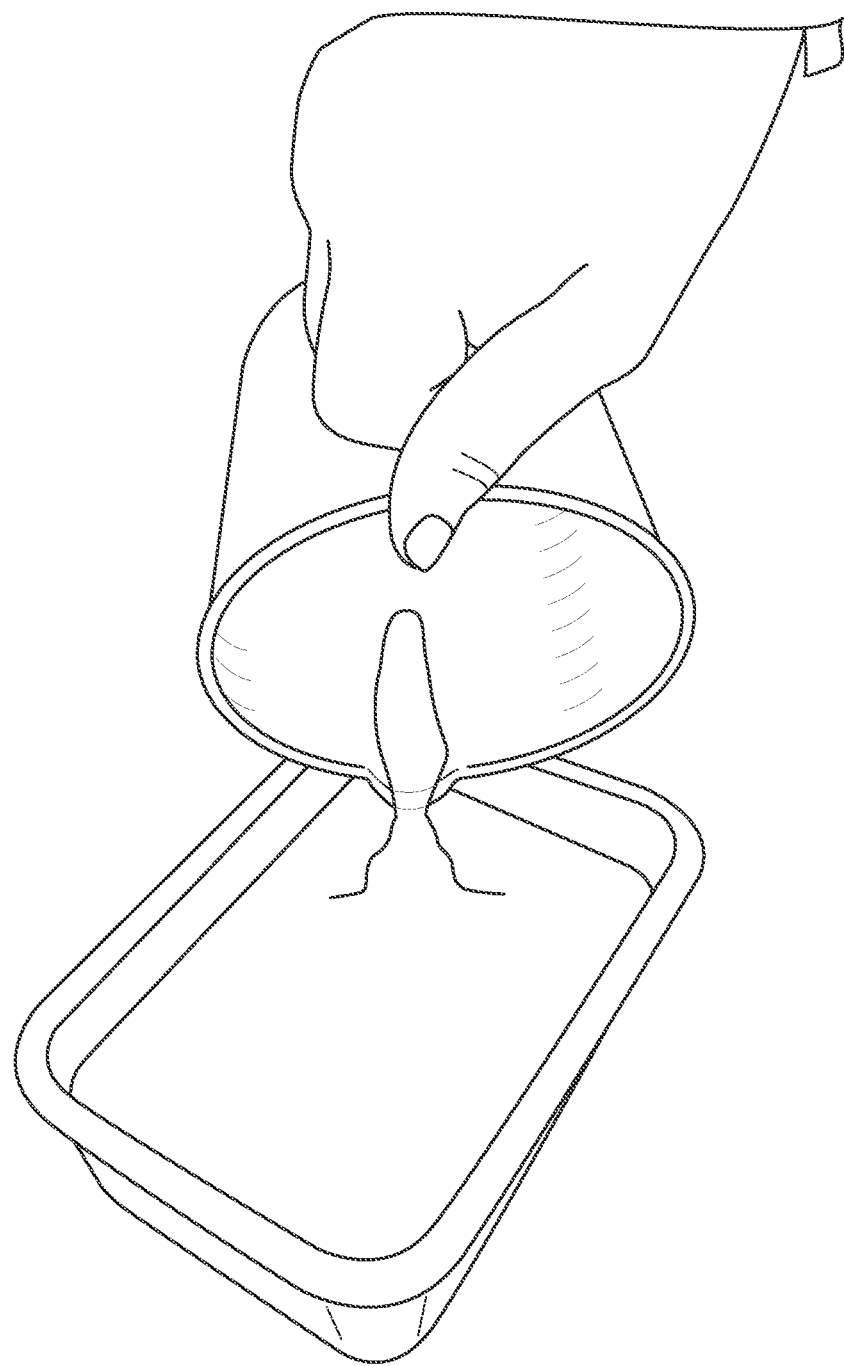
FIG. 25 shows the bulk suspension following transfer to a clean glass dish.

A copper-containing suspension was created by incubating 16 copper strips (3.625 inches×2.25 inches×0.3 inches) in 2 L of 0.9% sodium chloride buffered to approximately pH 5 by the addition of 0.016 g sodium phosphate monobasic anhydrous. The copper strips were separated by stainless steel rods as shown in FIG. 22. The 0.9% sodium chloride solution was placed into a closed borosilicate glass container in an oven heated to 37° C. and the copper strips and stainless steel rods (6 rods for every 8 copper strips) were placed into a glass dish and heated to 37° C. in the same oven. Once the sodium chloride solution reached a temperature of 37° C., the copper strips were placed into the saline solution and allowed to incubate for 24 hours±30 minutes. The copper strips and stainless steel rods were subsequently removed (FIG. 23), and the remaining suspension was measured and collected into clean glass containers for immediate use, as shown in FIGS. 24-25. As shown in FIGS. 23-25, precipitated copper salts form a sediment on the bottom of the container. The total measured volume of bulk suspension, including the precipitate was 32 oz.

Composition of the 3VM1001 Cream

This example provides an analysis of three of the 3VM1001 products: the bulk suspension used in the production of the 3VM1001 cream; a similar bulk suspension manufactured without the use of sodium phosphate, and the 3VM1001 cream itself. The bulk suspension is a combination of a liquid phase and a solid phase. If left to stand, the solid phase will form a precipitate at the bottom of the bulk container. The objective, in part, of the analyses performed, was to assess the amount of copper found in the liquid phase of the bulk suspension and the cream.

TABLE 10

Copper Composition of Bulk Suspension and 3VM1001 Cream

| Test Article | Liquid phase Composition | Cu in Liquid phase | Solid Phase Composition | Cu in Solid Phase |
| --- | --- | --- | --- | --- |
| Bulk suspension with phosphate | Sodium chloride | Below limit of detection (500 ppb) | Copper phosphate; copper hydroxide | 37 µg/mL |
| Bulk suspension without phosphate | Sodium chloride, copper chloride | 0.94 µg/mL | Copper hydroxide | 9.99 µg/mL |
| Cream | | 11.5 µg/mL | | 1.7 µg/mL |

Table 10 shows that the solubility of the copper in the liquid phase by more than 20-fold in the cream, compared to the bulk suspension. Cu is primarily present in the liquid phase of the cream at 11.5 µg/mL, compared to 500 ppb (0.5 µg/mL) for the bulk suspension with phosphate. Thus, the amount of copper present in the liquid phase is substantially enhanced in the 3VM1001 cream compared to the bulk suspension. This enhanced solubility was surprising and unexpected. Because dissolved copper is expected to have substantially greater bioavailability than a solid precipitate, this finding provides a rationale for the therapeutic effect of the 3VM1001 cream.

To prepare the 3VM1001 cream, the bulk suspension is combined with a cream base, such as VersaBase. Unless otherwise noted, the 3VM1001 cream comprises 30% bulk suspension. More dilute creams with a lower percentage of bulk suspension and correspondingly higher percentage of cream base were also prepared and tested, such as 3VM1001 20% (20% bulk suspension), 3VM1001 10% (10% bulk suspension), and 3VM1001 5% (5% bulk suspension). The composition of VersaBase is shown in Table 11, below.

The use of phosphate provides for a greater total copper concentration in the precipitate (37 µg/mL compared to about 10 µg/mL in the phosphate free bulk). See Table 10. Use of the phosphate bulk at a 30% concentration in the cream (which would be expected to produce a final concentration of about 11 µg/mL [30% of 37 µg/mL]) produces a copper cream product at a concentration of 11.5 µg/mL in the liquid phase.

Composition of the LUXSOL Gel

To prepare a gel for use in the present disclosure, the bulk suspension is combined with a gel base, such as VersaBase gel. The VersaBase gel consists of the following ingredients:
Water
Ammonium Acryloyldimethyltaurate/VP Copolymer
Aloe Barbadensis Leaf Juice Powder
Allantoin
Disodium EDTA
Methylchloroisothiazolinone
Methylisothiazolinone Unless otherwise noted, the LUXSOL gel comprises 30% bulk suspension. More dilute creams with a lower percentage of bulk suspension and correspondingly higher percentage of gel base were also prepared and tested, such as LUXSOL gel 20% (20% bulk suspension), LUXSOL gel % (10% bulk suspension), and LUXSOL gel 5% (5% bulk suspension).

Composition of the LUXSOL Suppository

To prepare the suppositories, the bulk suspension is combined with a suppository base comprising hydrogenated vegetable oil and PEG-8 distearate.

Unless otherwise noted, the LUXSOL Suppository comprises 30% bulk suspension. More dilute suppositories with a lower percentage of bulk suspension and correspondingly higher percentage of suppository base were also prepared and tested, such as LUXSOL Suppository 20% (20% bulk suspension), LUXSOL Suppository % (10% bulk suspension), and LUXSOL Suppository 5% (5% bulk suspension).

TABLE 11

VersaBase Cream Quantitative Composition

| INCI Name (Chemical Name) | % | Trade Name | Manufacturer |
| --- | --- | --- | --- |
| Water | 71.08% | N/A | N/A |
| Emulsifying Wax NF | 11.00% | Polawax NF-PA-(MH) | Croda Inc. |
| Ethylhexyl Stearate | 8.00% | Lexol EHS | Inolex Inc./Nexeo |
| Cyclopentasiloxane | 5.00% | Xiameter ® PMX-0245 Cyclopentasiloxane | Xiameter ® from Dow Corning/Univar USA |
| Sorbitol USP FCC | 4.00% | Sorbo ® Sorbitol Solution USP/FCC | Ingredion/Univar Chicago |
| Tocopheryl Acetate USP | 0.50% | DL-A-Tocopheryl Acetate | DSM Nutritional Products |
| Aloe Barbadensis Leaf Juice Powder | 0.20% | Aloe Vera Gel Freeze Dried Powder 200: 1 Extract-Micronized | Aloe Vera of California Inc. |
| Disodium EDTA USP FCC JECFA | 0.18% | Versene ™ NA Chelating Agent | Dow Chemical Company/Univar USA |
| Methylchloroisothiazolinone Methylisothiazolinone | 0.04% | Kathon ™ CG Preservative | Rohm and Haas Chemicals LLC |

Example 35

The systemic and dermal toxicity and toxicokinetics of 3VM1001 cream were evaluated following 30 days of 4-times daily topical administration to Sprague Dawley rats, followed by a 2-week recovery period.

The objective of this study was to evaluate the systemic and dermal toxicity and toxicokinetics of the test article following 30 days of 4-times daily topical administration to Sprague Dawley rats, followed by a 2-week recovery period.

A total of 92 rats (46 males and 46 females) were randomized into 2 treatment groups, including a vehicle control group (Group 1) and one test article group (Group 2). Each group included a toxicity portion with 2 cohorts (main and recovery) and a toxicokinetic (TK) portion. Animals received a topical administration of either vehicle cream (Group 1) or test cream (3VM1001 cream—Group 2) 4 times daily for 30 consecutive days. Blood samples for TK analysis were collected on study Day 1 (1 time point for control group and 6 time points for test group) and study Day 30 (1 time point for control group and 7 time points for test group) from TK animals. Main study animals (10 animals/gender/group) were euthanized on Day 31 and recovery animals (5 animals/gender/group) were euthanized on Day 44 following a 2-week period without treatment.

higher in male recovery animals), and no gross or microscopic pathology findings that were attributable to test article exposure.

The TK results indicated that there was no Cu absorption or accumulation after 30 consecutive days of four times daily topical administration of 3VM1001 cream. The quantifiable serum Cu concentrations in Group 2 3VM1001 cream (test) animals were similar to or less than those of Group 1 3VM1002 cream (vehicle control). 3VM1002 has the same composition as 3VM1001, except that it lacks copper ions In conclusion, the no observable effect level for 3VM1001 cream applied topically to Sprague Dawley rats four times daily for 30 consecutive days is greater than or equal to 18 µg copper/kg/day.

Example 36

The objective of this study was to evaluate the systemic and dermal toxicity and toxicokinetics of 3VM1001 cream following topical administration to Hanford minipigs, followed by a 2-week recovery period.

Two groups of miniature swine, each containing 12 animals (6 animals per gender) were successfully treated with

TABLE 12

| Group | No. of Animals/Sex (Recovery) Main | TK | Treatment (Cu conc. as µg/mL) | Dose Amount [b] (mL/kg/dose) | No. of Daily Doses | Target Dose Level [c] (µg Cu/kg/day) | Calculated Dose Level [d] (µg Cu/kg/day) |
|---|---|---|---|---|---|---|---|
| 1 (Vehicle) | 10 (5) | 3 + 1 | 3VM1002 Vehicle Cream (0) | 0.33 | 4 | 0 | 0 |
| 2 | 10 (5) | 9 + 1 | 3VM1001 Cream (12) [a] | 0.33 | 4 | 14.4 | 18-20 |

Note:

The actual density of test article was determined to be 1 g of cream = ~1.1 mL instead of 1 mL as claimed; The actual dose level was calculated based on the provided CoAs (concentration: 17 µg copper/g at predose and 15 µg copper/g at post dose).

[a] Nominal copper concentration.

[b] Dose amount was increased from 0.3 mL/kg/dose to 0.33 mL/kg/dose (Protocol Amendment 2).

[c] Target dose level (µg Cu/kg/day) = 3.6 (µg Cu/kg/dose) × 4 (times/day).

[d] See Table 6 for an explanation.

All animals were dosed appropriately during the study. There were no unscheduled deaths or significant moribundity for any animal. There were no findings during physical examinations, clinical observations or dose site Draize scoring that indicated an adverse effect of test article exposure. Animals consumed food normally each day, and gained weight during the study, without significant differences in body weight between groups at any time point. Between-group differences in clinical pathology parameters (hematology, serum chemistry) were of low magnitude, and consistent with normal biologic variation. There were no important differences in organ weights (only kidney weight either vehicle control (3VM1002 cream—Group 1) or the test article (3VM1001 cream (containing copper, Cu)—Group 2), administered topically 4 times daily for 30 consecutive days. Two animals per gender per group were followed for an additional 2 weeks without treatment. Animals were evaluated for signs of toxicity through physical examinations, clinical observations, body weight and body weight change, dose site Draize scoring, clinical pathology (hematology, coagulation, serum chemistry and urinalysis), electrocardiography, ophthalmology, organ weight and histopathology. Toxicokinetic characteristics were assessed on study Day 1 and Day 30.

TABLE 13

| Group | No. of Animals (Recovery) Male | No. of Animals (Recovery) Female | Treatment (Cu conc. as μg/g) | Dose Amount[b] (mL/kg/dose) | No. of Daily Doses | Target Dose Level[c] (μg Cu/kg/day) | Calculated Dose Level[d] (μg Cu/kg/day) |
|---|---|---|---|---|---|---|---|
| 1 (Vehicle) | 4 (2) | 4 (2) | 3VM1002 Vehicle Cream (0) | 0.33 | 4 | 0 | 0 |
| 2 | 4 (2) | 4 (2) | 3VM1001 Cream (12)[a] | 0.33 | 4 | 14.4 | 18-20 |

Note:
The actual density of test article was determined to be 1 g of cream = 1.1 mL instead of claimed as 1 g of cream = 1 mL; The actual dose level was calculated based on the provided CoAs (concentration: 17 μg copper/g at predose and 15 μg copper/g at post dose).
[a]Nominal copper concentration.
[b]Dose amount was increased from 0.3 mL/kg/dose to 0.33 mL/kg/dose on Day 3 (Protocol Amendment 2, Appendix I).
[c] Target dose level (ug Cu/kg/day) = 3.6 (μg Cu/kg/dose) × 4 (times/day).
[d] See Table 6 for an explanation.

All animals were dosed appropriately during the study. There were no unscheduled deaths or significant moribundity for any animal. There were no findings during physical examinations, clinical observations or dose site Draize scoring that indicated an adverse effect of test article exposure. Animals generally consumed all food offered each day, and gained weight during the study, without significant differences in body weight between groups at any time point. There were no test article associated findings with respect to electrocardiography or ophthalmology assessments. Between-group differences in clinical pathology parameters (hematology, coagulation, serum chemistry and urinalysis) were of low magnitude, and consistent with normal biologic variation. There were no important differences in organ weights, and no gross or microscopic pathology findings that were attributable to test article exposure.

Serum Cu concentrations (TK) were determined for control animals (1 hour postdose), 7 time points in test animals on study Day 1 and Day 30 and on termination days on 31 and 44. The TK results indicated that there was no Cu absorption or accumulation after 30 consecutive days of four times daily topical administration of 3VM1001 cream. The quantifiable serum Cu concentrations in Group 2 3VM1001 cream (test) animals were similar to or less than those of Group 1 3VM1002 cream (vehicle control).

In conclusion, the no observable effect level for 3VM1001 cream administered topically to miniature swine four times daily for 30 consecutive days is greater than or equal to 18 μg copper/kg/day.

Example 37

A suspension consisting of 46 μg/mL of copper in 0.9% normal saline with 0.8 g/L NaPO$_4$ added for pH adjustment (referred to herein as 3VM1000) was evaluated for the potential to induce chromosome aberrations in HPBL during short (3-hour) and long (22-hour) incubations with or without an exogenous metabolic activation system.

HPBL cultures were treated with the test article, positive control, or vehicle control in the presence and absence of an Aroclor™ 1254-induced rat liver S9 microsomal fraction. The saline concentration in the culture medium was 10% v/v. 3VM1000 concentrations tested in the range-finding assay ranged from 1%-10% v/v in culture, up to the highest feasible concentration dosing 10% of the provided solution. Precipitates were observed at the end of treatment at 10% in each treatment. Based on cytotoxicity (i.e., reduction in mitotic index) observed in the range-finding assay, concentrations used during the chromosome aberration assay ranged from 2%-10% v/v in culture.

The concentrations selected for evaluation of chromosome aberrations in the aberration assay were based on precipitates and are as follows: a) 3-hour treatment without metabolic activation, 4%, 6% (highest concentration tested without precipitates), and 8% (lowest concentration tested with precipitates); b) 22-hour treatment, 6%, 8% (highest concentration tested without precipitates), and 10% (lowest concentration tested with precipitates); and c) 3-hour treatment with activation, 2%, 4% (highest concentration tested without precipitates), and 6% (lowest concentration tested with precipitates). These cultures, along with the vehicle and 1 concentration of positive control for each treatment condition, were analyzed for aberrations. Structural chromosome aberrations were scored for each concentration from a total of 300 metaphase cells (when possible) or >50 aberrant cells. Numerical aberrations were evaluated in 400 metaphase cells per concentration.

No statistically significant differences in the percent of cells with structural chromosome aberrations or the percent of cells with greater than 1 aberration were noted under any assay condition. In addition, there was no statistically significant test article-related increase in numerical aberrations (polyploidy or endoreduplication) in any treatment compared to the vehicle controls. The data from the vehicle, negative, and positive controls demonstrated the validity and sensitivity of this test system.

3VM1000 was considered negative for inducing structural aberrations in HPBL with or without metabolic activation under the conditions of this test system. In addition, no statistically significant increases in numerical aberrations (polyploidy or endoreduplication) were observed in 3VM1000-treated cultures.

Example 38

The objective of this study was to assess the potential of the test article to induce micronuclei in polychromatic erythrocytes (PCEs) in rat bone marrow following 3 consecutive days of treatment administered by oral gavage. This assay evaluated compounds for in vivo clastogenic activity and/or disruption of the mitotic apparatus.

3VM1000 in the vehicle (0.9% sodium chloride, USP) was administered orally by gavage once daily for 3 consecutive days to 3 groups (Groups 2-4) of Crl:CD(SD) rats. Dosage levels were 0.046, 0.153, and 0.46 mg/kg/day for Groups 2, 3, and 4, respectively. A concurrent vehicle control group (Group 1) received the vehicle on a comparable regimen. A positive control group (Group 5) received a single oral dose of 60 mg/kg cyclophosphamide monohydrate (CPS) on study day 2, the day prior to the scheduled euthanasia. The dose volume was 10 mL/kg for all groups. Each group consisted of 6 animals/sex. All animals were euthanized on study day 3, at approximately 18-24 hours following dose administration for Groups 1-4 and at approximately 24 hours following dose administration for Group 5, and discarded following bone marrow collection.

All animals were observed twice daily for mortality and moribundity. Detailed physical examinations were performed and individual body weights were recorded weekly (±2 days) during acclimation, on the day of randomization, on study day 0 (prior to dosing), on study day 2 (last day of dosing), and on the day of the scheduled euthanasia. Clinical examinations were performed at the time of dose administration and 1-2 hours following dose administration. Individual food weights were recorded weekly (±2 days) during acclimation, on the day of randomization, on study day 0, and on the day of the scheduled euthanasia. Bone marrow collection for micronucleus evaluation was performed for 5 of 6 animals/sex/group at the scheduled euthanasia (study day 3). All animals were discarded without necropsy at the scheduled euthanasia. Bone marrow smears were prepared and the coded slides were counted for polychromatic, normochromatic, and micronucleated polychromatic erythrocytes following the final bone marrow sample collection on study day 3.

All animals survived to the scheduled euthanasia. There were no test article-related clinical observations or effects on body weights or food consumption. 3VM1000 did not produce an increase in the mean number of micronucleated polychromatic erythrocytes (MN-PCEs) compared to the vehicle control group. No bone marrow cytotoxicity (decreases in the ratio of polychromatic to total erythrocytes, PCE:TE ratio) was noted in any test article-treated group. Therefore, 3VM1000 met the criteria for a negative response for bone marrow cytotoxicity and clastogenicity under the conditions of this assay.

Based on the results of this study, oral administration of 3VM1000 once daily to Crl:CD(SD) rats for 3 consecutive days resulted in a negative response for induction of bone marrow micronuclei at dosage levels up to 0.46 mg/kg/day.

Example 39

The objective of this study was to determine the potential of 3VM1001 cream to produce a skin sensitization reaction following dermal topical administrations (induction exposures) followed by a challenge dose to young adult guinea pigs.

This study was conducted with thirty-nine (39) healthy female young adult guinea pigs. Twenty one (21) animals were administered with 3VM1001 cream, seven (7) animals were administered with DNCB (dinitro-chloro-benzene) as positive controls and eleven (11) animals were administered with 3VM1002 cream, the vehicle cream, as negative controls. There were two test phases (induction and challenge phase) in the proposed experiment. In the induction phase (Day 1), each animal was topically administered with either test or control substance on the flank area for 6±0.5 hours. The same procedure was performed three (3) times per week for three (3) consecutive weeks for the two control groups and the test group. For the challenge phase (Day 32), the untreated flank areas of test and control animals were topically administered with the appropriate amount of test or control substance using an occlusion patch for 6±0.5 hours. Dermal irritation was scored at 24±2 and 48±2 hours post challenge phase patch removal.

No skin irritation was observed to be associated with administration of the test or control cream at either scoring time points (24 or 48 hours).

In conclusion, the 3VM1001 cream did not cause skin sensitization reaction under the conditions of this study.

Example 40

In this example, an appropriate amount of copper ion-containing suspension, such as 3VM1000, is combined with a toothpaste base material to form a copper ion toothpaste in which the copper ion-containing solution constitutes in the range of 5 percent to 30 percent of the total weight of the copper ion toothpaste.

The toothpaste base material can be a commercially available toothpaste including any of the toothpastes marketed and sold under the major brand names. A toothpaste made in accordance with Example 40 is advantageous for reducing and/or preventing the symptoms of radiation damage (e.g. radiation dermatitis) affecting the mouth, preventing biofilm (plaque), treating bad breath, sore gums, gum disease and tooth decay when used on a daily basis in place of a person's regular toothpaste.

Example 41

In this study, the 3VM1000 copper ion-containing suspension was used as a mouthwash to prevent biofilm formation (plaque) in two individuals. Specifically, one tablespoon of 3VM1000 was as a mouthwash once a day for one minute, over the course of one year. Oral examinations every three months showed that both individuals were 99-100% plaque free throughout the course of the treatment.

The invention claimed is:

1. A method of preventing or treating radiation damage in a subject in need thereof, the method comprising administering a suspension to the subject in a therapeutically effective amount, the suspension consisting of:
   a. copper ions leached from a solid copper metal;
   b. a saline solution; and
   c. one or more buffers,
   wherein the copper ions are suspended in the saline solution, and wherein the copper ions constitute between about 0.0002% and about 0.00627% by weight of the suspension.

2. The method of claim 1, wherein the radiation damage is caused by radiation therapy.

3. The method of claim 1, wherein the radiation damage is radiation dermatitis.

4. The method of claim 1, wherein the copper ions constitute about 46 milligrams per 7.44 fluid ounces of the suspension, or about 0.209 milligrams per milliliter, about 35 milligrams per 7.44 fluid ounces of the suspension, or about 0.159 milligrams per milliliter, about 22 milligrams per 7.44 fluid ounces of the suspension, or about 0.100 milligrams per milliliter, or about 8.8 milligrams per 7.44 fluid ounces of the suspension, or about 0.0400 milligrams per milliliter.

5. The method of claim 1, further comprising:
   a. before administering one or more administrations of the suspension to the subject, obtaining a first condition score from the subject; and
   b. after administering one or more administrations of the suspension to the subject, obtaining a second condition score from the subject, wherein the second condition score is less than the first condition score.

6. The method of claim 5, wherein the first and second condition scores are VAS scores, WOMAC scores, RTOG scores, Catterall scale scores, or Likert scale scores.

7. A method of preventing or treating radiation damage in a subject in need thereof, the method comprising administering a formulation to the subject in a therapeutically effective amount, the formulation comprising a base and a suspension, wherein the base is a lotion base, a gel base, a cream base, or a foam base, wherein the suspension consists of:
   a. copper ions leached from a solid copper metal;
   b. a saline solution; and
   c. one or more buffers;
   wherein the copper ions are suspended in the saline solution, and wherein the copper ions constitute between about 0.0002% and about 0.00627% by weight of the suspension.

8. The method of claim 7, wherein the radiation damage is caused by radiation therapy.

9. The method of claim 7, wherein the radiation damage is radiation dermatitis.

10. The method of claim 1, wherein the copper ions are leached into the saline solution from the solid copper metal by:
   a. placing the solid copper metal in the saline solution;
   b. allowing the solid copper metal to remain in the saline solution for a predetermined period of time, during which predetermined period of time the copper ions leach into the saline solution; and
   c. removing the solid copper metal from the saline solution after the predetermined period of time.

11. The method of claim 7, wherein the copper ions are leached into the saline solution from the solid copper metal by:
   a. placing the solid copper metal in the saline solution;
   b. allowing the solid copper metal to remain in the saline solution for a predetermined period of time, during which predetermined period of time the copper ions leach into the saline solution; and
   c. removing the solid copper metal from the saline solution after the predetermined period of time.

12. The method of claim 1, wherein the one or more buffers comprises one or more of acetate and acetic acid.

13. The method of claim 1, wherein the one or more buffers comprises one or more of phosphate and phosphoric acid.

14. The method of claim 7, wherein the one or more buffers comprises one or more of acetate and acetic acid.

15. The method of claim 7, wherein the one or more buffers comprises one or more of phosphate and phosphoric acid.

16. The method of claim 1, wherein the suspension comprises at least about 10-15 µg/mL of copper ions.

17. The method of claim 7, wherein the formulation comprises at least about 10-15 µg/mL of copper ions.

18. The method of claim 7, wherein the base is a cream base, and wherein the cream base comprises:
   (A) water,
   (B) emulsifying wax,
   (C) ethylhexyl stearate,
   (D) cyclopentasiloxane,
   (E) sorbitol, and
   (F) tocopheryl acetate.

19. The method of claim 1, wherein the method is a method of treating radiation damage in the subject in need thereof.

20. The method of claim 1, wherein the method is a method of preventing radiation damage in the subject in need thereof.

21. The method of claim 7, wherein the method is a method of treating radiation damage in the subject in need thereof.

22. The method of claim 7, wherein the method is a method of preventing radiation damage in the subject in need thereof.

23. The method of claim 1, wherein the copper ions are not leached from a copper salt.

24. The method of claim 7, wherein the copper ions are not leached from a copper salt.

25. The method of claim 1, wherein the suspension has a pH of 5±0.4.

26. The method of claim 7, wherein the suspension has a pH of 5±0.4.

27. The method of claim 1, wherein the solid copper metal is a pure copper metal.

28. The method of claim 7, wherein the solid copper metal is a pure copper metal.

29. The method of claim 1, wherein the solid copper metal is a copper alloy.

30. The method of claim 7, wherein the solid copper metal is a copper alloy.

\* \* \* \* \*